United States Patent
Nishizawa et al.

(10) Patent No.: US 8,921,084 B2
(45) Date of Patent: Dec. 30, 2014

(54) PROTEIN-ENCLOSED CARBON NANOTUBE FILM, AND SENSOR AND POWER-GENERATING DEVICE EACH EQUIPPED WITH THE CARBON NANOTUBE FILM AS ELECTRODE

(71) Applicants: Tohoku University, Sendai (JP); National Institute of Advanced Industrial Science and Technology, Tokyo (JP)

(72) Inventors: Matsuhiko Nishizawa, Sendai (JP); Takeo Miyake, Sendai (JP); Syuhei Yoshino, Sendai (JP); Takeo Yamada, Tsukuba (JP); Kenji Hata, Tsukuba (JP)

(73) Assignees: Tohoku University, Sendai-Shi, Miyagi (JP); National Institute of Advanced Industrial Science and Technology, Tokyo (JP)

( * ) Notice: Subject to any disclaimer, the term of this patent is extended or adjusted under 35 U.S.C. 154(b) by 121 days.

(21) Appl. No.: 13/727,042

(22) Filed: Dec. 26, 2012

(65) Prior Publication Data
US 2013/0130230 A1 May 23, 2013

Related U.S. Application Data

(63) Continuation of application No. PCT/JP2011/064594, filed on Jun. 24, 2011.

(30) Foreign Application Priority Data

Jun. 29, 2010 (JP) ................................. 2010-148068
Oct. 6, 2010 (JP) ................................. 2010-227013

(51) Int. Cl.
| | | |
|---|---|---|
| C12N 9/00 | (2006.01) | |
| H01M 8/16 | (2006.01) | |
| B82Y 30/00 | (2011.01) | |
| B82Y 40/00 | (2011.01) | |
| C01B 31/02 | (2006.01) | |
| G01N 27/327 | (2006.01) | |
| H01M 4/88 | (2006.01) | |
| H01M 4/90 | (2006.01) | |

(52) U.S. Cl.
CPC . *C12N 9/00* (2013.01); *B82Y 30/00* (2013.01); *B82Y 40/00* (2013.01); *C01B 31/0286* (2013.01); *G01N 27/3278* (2013.01); *H01M 4/8846* (2013.01); *H01M 4/9083* (2013.01); *C01B 2202/04* (2013.01); *C01B 2202/08* (2013.01); *C01B 2202/34* (2013.01); *H01M 8/16* (2013.01); *Y02E 60/50* (2013.01); *Y10S 977/705* (2013.01); *Y10S 977/714* (2013.01); *Y10S 977/737* (2013.01); *Y10S 977/747* (2013.01); *Y10S 977/755* (2013.01)

USPC ............. 435/183; 435/4; 435/189; 977/705; 977/714; 977/737; 977/747; 977/755

(58) Field of Classification Search
USPC .............. 435/4, 183, 189; 977/705, 714, 737, 977/747, 752
See application file for complete search history.

(56) References Cited

U.S. PATENT DOCUMENTS

| | | |
|---|---|---|
| 2002/0177032 A1 | 11/2002 | Suenaga et al. |
| 2007/0062821 A1 | 3/2007 | Sato et al. |
| 2009/0214847 A1 | 8/2009 | Maruyama et al. |
| 2010/0068461 A1 | 3/2010 | Wallace et al. |

FOREIGN PATENT DOCUMENTS

| | | |
|---|---|---|
| JP | 2003-200052 A | 7/2003 |
| JP | 2007-035437 A | 2/2007 |
| JP | 2007-182342 A | 7/2007 |
| JP | 2009-222459 A | 10/2009 |
| JP | 2009-541198 A | 11/2009 |

OTHER PUBLICATIONS

Qiu et al. 2007. A Nanocomposite Chitosan Based on Ferrocene-Modified Silica Nanoparticles and Carbon Nanotubes for Biosensor Application. Electroanalysis, vol. 19, No. 22, pp. 2335-2341.*
Pang et al. 2010.Amperometric Detection of Glucose Using a Conjugated Polyelectrolyte Complex with Single-Walled Carbon Nanotubes. Macromolecules, vol. 43, pp. 10376-10381.*
International Search Report in PCT/JP2011/064594 dated Aug. 19, 2011.
International Preliminary Examination Report in PCT/JP2011/064594 dated Jan. 8, 2012.
Chew Khim Tan, Kian Ping Loh & Thong T. L. John, "Direct amperometric detection of glucose on a multiple-branching carbon nanotube forest," The Royal Society of Chemistry 2008, pp. 448-451, Feb. 18, 2008.
Eugenii Katz & Itamar Willner, "Biomolecule-Functionalized Carbon Nanotubes: Applications in Nanobioelectronics," ChemPhysChem 2004, pp. 1084-1104, May 2004.

* cited by examiner

*Primary Examiner* — Jon P Weber
*Assistant Examiner* — Kailash C Srivastava
(74) *Attorney, Agent, or Firm* — Lowe Hauptman & Ham, LLP

(57) ABSTRACT

The present invention answers the demands of power generating device and biosensor development and provides a flexible, free-standing type protein containing carbon nanotube film, and a sensor and power generating device each equipped with the carbon nanotube film as an electrode. According to the present invention a carbon nanotube free standing film is provided including a carbon nanotube aggregate formed by aggregating a plurality of carbon nanotubes, and a plurality of enzymes included between the plurality of carbon nanotubes. The carbon nanotube film may include a different protein to the enzyme and may include a surfactant agent between the plurality of carbon nanotubes.

7 Claims, 23 Drawing Sheets

FIG. 4
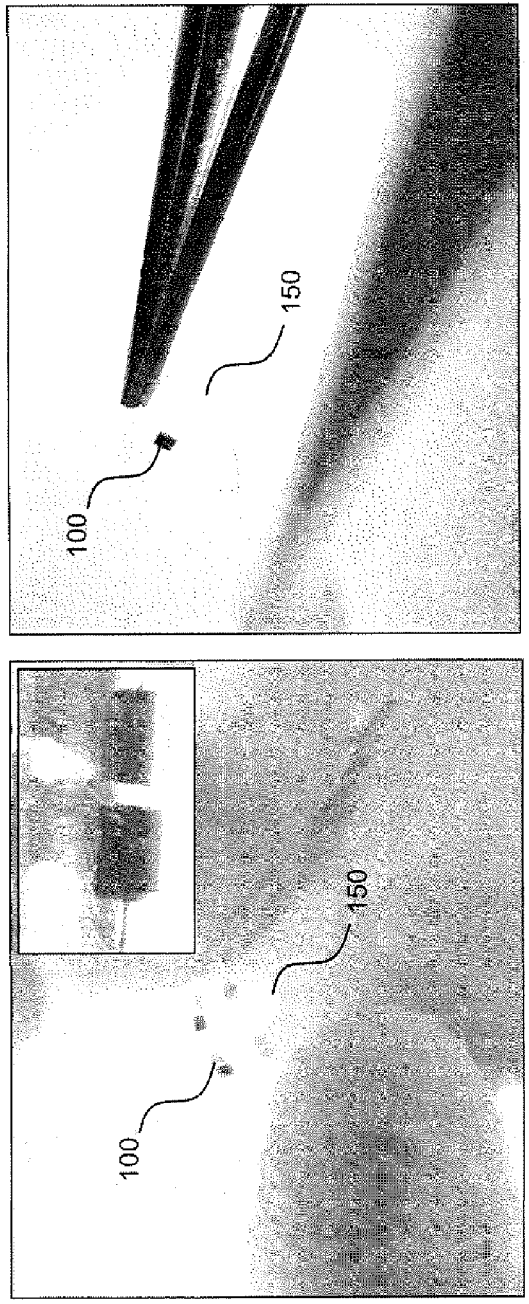
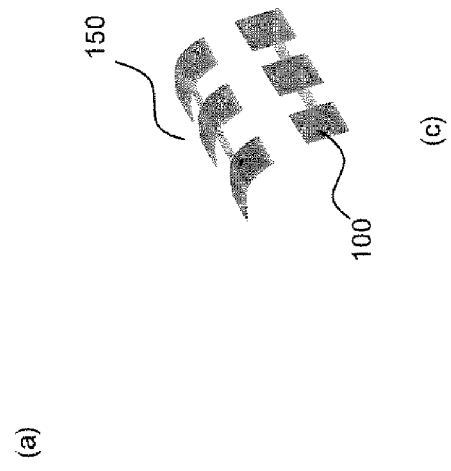

FIG. 8
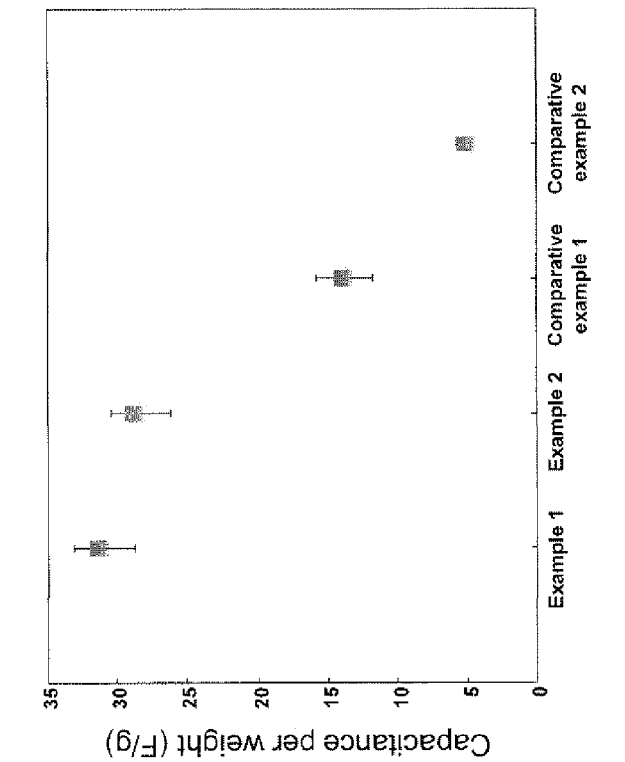
(b)
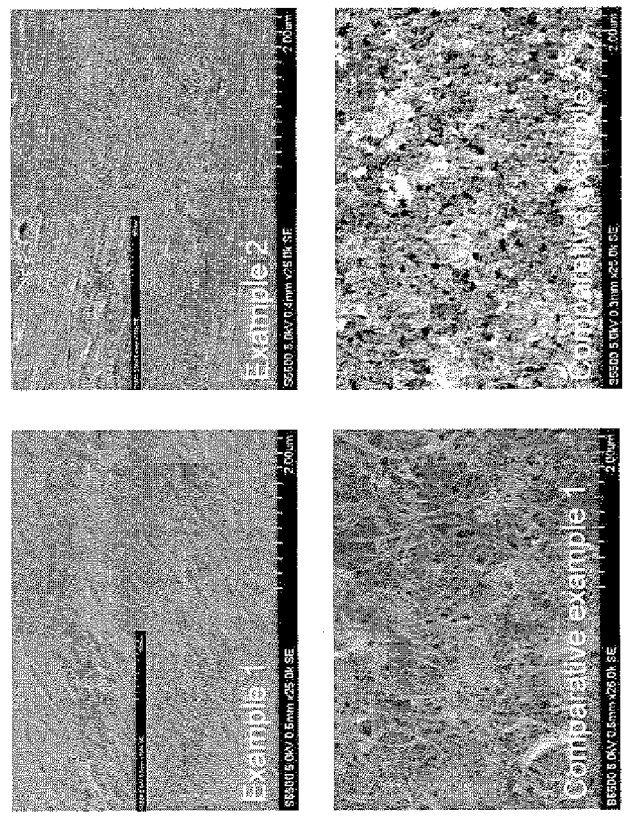
(a)

PROTEIN-ENCLOSED CARBON NANOTUBE FILM, AND SENSOR AND POWER-GENERATING DEVICE EACH EQUIPPED WITH THE CARBON NANOTUBE FILM AS ELECTRODE

CROSS REFERENCE TO RELATED APPLICATIONS

This application is based upon and claims the benefit of priority from the prior Japanese Patent Application No. 2010-148068, filed on Jun. 29, 2010, the prior Japanese Patent Application No. 2010-227013, filed on Oct. 6, 2010, and PCT Application No. PCT/JP2011/064594, filed on Jun. 24, 2011, the entire contents of which are incorporated herein by reference.

FIELD

The present invention is related to a protein-enclosed carbon nanotube aggregate (called a Carbon Nanotube Forest; CNTF) free standing film. In particular, the present invention is related to a free standing film of a carbon nanotube aggregate containing a protein such as an enzyme and a sensor and a power generating device used in the film for an electrode and a manufacturing method of the same. Here, a free standing film refers to a film which does not require a support substrate.

BACKGROUND

In recent years, beginning with environmental problems power generation devices with a low environmental burden are being demanded. In addition, together with the development circumstances of electronic paper or bio-electronic devices such as health monitoring which are dominant as a near future device, the demand for next generation power generation devices continues to head towards to conventional safety and light weight as well as clean, flexible and small scale devices. Given these circumstances, since a biofuel cell which generates power using a fuel derived from living matter also includes much appeal (close biofuel (sugars, alcohol), mild operating environment (normal temperature, neutrality, atmosphere), unnecessary fuel refinement and unnecessary separator etc), they are attracting attention worldwide.

A biofuel cell is a type of fuel cell which includes a structure in which an enzyme which oxidizes a fuel derived from living matter is fixed to an anode electrode, an enzyme which reduces an enzyme is fixed to a cathode electrode and electrical energy is obtained from a fuel derived from living matter using an oxidation reduction reaction by these enzymes.

However, there are many problems in the material, components and packaging technology of a biofuel cell derived from a chemical battery or a biosensor. Because an electrode material with carbon as constituent element has excellent safety, durability and biocompatibility, it is used widely in sensors or batteries and is usually attached to carbon fine particles using a binder. For example, a procedure in which low temperature firing carbon fine particles are adsorbed on an electrode and an enzyme is fixed to the inner space or external surface of the fine particles is reported in Japanese Laid Open Patent 2007-34537. However, pore size in which matches the size of a protein can't be controlled and there is no flexibility. In addition, enzyme fixing to a carbon nanotube aggregate orientated in a perpendicular direction on a substrate is previously reported by the inventors in Japanese Laid Open Patent 2009-222459 or in non-Japanese Laid Open Patent 2007-34537, and an enzyme modification to a carbon nano-fiber is reported in non-Japanese Laid Open Patent 2009-222459. However, in each of these reports the carbon nanotube aggregate integrally formed with a support and does not contain flexibility.

SUMMARY

If capabilities such as safety, small scale and flexibility can be provided to an electrode, the design freedom of a power generating device can be improved and the performance of a battery is advanced. In addition, these electrode capabilities are commonly demanded for a biosensor and significantly contribute to the development of biosensors.

The present invention answers the demands of power generating devices and biosensor development and provides a flexible, free-standing type protein containing carbon nanotube film, and a sensor and power generating device each equipped with the carbon nanotube film as an electrode.

(1) According to the present invention a carbon nanotube free standing film is provided including a carbon nanotube aggregate formed by aggregating a plurality of carbon nanotubes, and a plurality of enzymes included between the plurality of carbon nanotubes.

(2) The carbon nanotube free standing film may include a different protein to the enzyme.

(3) The carbon nanotube free standing film may include a surfactant agent between the plurality of carbon nanotubes.

(4) The carbon nanotube free standing film according to claim 1, wherein a plurality of mediator molecules is included between the plurality of carbon nanotubes.

(5) The enzyme may be oxidase or a dehydrogenase.

(6) The carbon nanotube aggregate may include a surface area of 600 $m^2/g$ or more and 2,600 $m^2/g$ or less, a weight density of 0.002 $g/cm^3$ or more and 0.2 $g/cm^3$ or less, and a pore size distribution maximum of 5 nm or more and 100 nm or less.

(7) A part may be included in which the enzyme is arranged in one column in a parallel direction to a length direction of the carbon nanotube at a space enclosed by 4 of the carbon nanotubes of the carbon nanotube aggregate.

(8) In addition, according to the present invention a fuel cell is provide including a pair of electrodes including the carbon nanotube free standing film according to any one of (1) to (7) and a fuel.

(9) In addition, according to the present invention a biosensor is provided including an electrode including the carbon nanotube free standing film according to any one of (1) to (7).

(10) In addition, according to the present invention a method of manufacturing a carbon nanotube free standing film is provided including peeling a carbon nanotube film including a plurality of carbon nanotubes grown on a substrate from the substrate, and immersing the carbon nanotube film in a solution including an enzyme.

(11) In the method of manufacturing the carbon nanotube free standing film, after peeling the carbon nanotube film from the substrate the carbon nanotube film may be immersed in a first buffer solution including a surfactant and next the carbon nanotube film may be immersed in the solution including the enzyme.

(12) In the method of manufacturing the carbon nanotube free standing film after the carbon nanotube film is immersed in the solution the carbon nanotube film may be dried.

(13) In the method of manufacturing the carbon nanotube free standing film the solution may include a different protein to the enzyme.

(14) in the method of manufacturing the carbon nanotube free standing film a plurality of mediator molecules may be included in the solution.

(15) In the method of manufacturing the carbon nanotube free standing film the enzyme may be an oxidase or a dehydrogenase.

(16) In the method of manufacturing the carbon nanotube free standing film the solution including the enzyme may be a concentration including a part in which the enzyme is arranged in one column in a parallel direction to a length direction of the carbon nanotube at a space enclosed by 4 of the carbon nanotubes of carbon nanotube aggregate.

BRIEF EXPLANATION OF THE DRAWINGS

FIG. 4 shows an example whereby the carbon nanotube film 100 related to one embodiment of the present invention is attached to a flexible substrate 150, (a) is an optical photograph and (b) is an exemplary view;

FIG. 8 shows the result of a capacitance evaluation in the examples and comparative examples (a) shows an electron microscopic image (SEM image) of a carbon nanotube film and (b) shows the result of the capacitance evaluation;

DESCRIPTION OF EMBODIMENTS

A protein containing carbon nanotube film, and a sensor and power generating device each equipped with the carbon nanotube film as an electrode related to the present invention and a method of manufacturing the same are explained below while referring to the diagrams. The protein containing carbon nanotube film, sensor and power generating device each equipped with the carbon nanotube film as an electrode related to the present invention includes an electrode which includes a carbon nanotube aggregate. The protein containing carbon nanotube film, sensor and power generating device each equipped with the carbon nanotube film as an electrode related to the present invention and method of manufacturing the same should not be interpreted as being limited to the descriptive content of the embodiments and examples shown below. Furthermore, in the diagrams which are referred to by the present embodiment and the examples described herein, the same reference symbols are attached to the parts having the same or similar functions and therefore repeating explanations are omitted.

The inventors of the present invention made keen examinations for realizing a safe, small scale and flexible, freestanding type protein containing carbon nanotube film, and a sensor and power generating device each equipped with the carbon nanotube film as an electrode. As a result, the inventors arrived at providing a flexible carbon nanotube film with improved battery capabilities, a sensor and power generating device each equipped with the carbon nanotube film as an electrode by fixing a fragile enzyme to a carbon nanotube aggregate which is an excellent conductive material using a mild fixing method.

The inventors of the present invention conducted research into a CNT structure having a high orientation using a Chemical Vapor Deposition method (referred to as CVD below), for example, they reported on a single-walled CNT structure and manufacturing method thereof in Science 306, 1362-1364 (2004) and International Published Patent WO2006/011655. In addition, they also reported on double-walled CNT (referred to as double-walled CNT below) structures and manufacturing method thereof in Nature Nanotechnology 1, 131-136 (2006) and Japanese Laid Open Patent 2007-145634.

The inventors of the present invention reported in Japanese Laid Open Patent 2009-222459 of realizing a highly efficient hydrogen generating device by making it possible for an electrode material in which an oxidation-reduction protein is fixed to an aggregate of an orientated single-walled CNT formed on a semiconductor substrate using the CVD (referred to as supper growth method below) described above, to efficiently accept electrons between the CNT and the oxidation-reduction protein. However, because a conductive substrate is used in Japanese Laid Open Patent 2009-222459, further improvement is necessary to realize a small scale and flexible free-standing carbon nanotube film.

First Embodiment (Carbon Nanotube Film)

Figure 1:
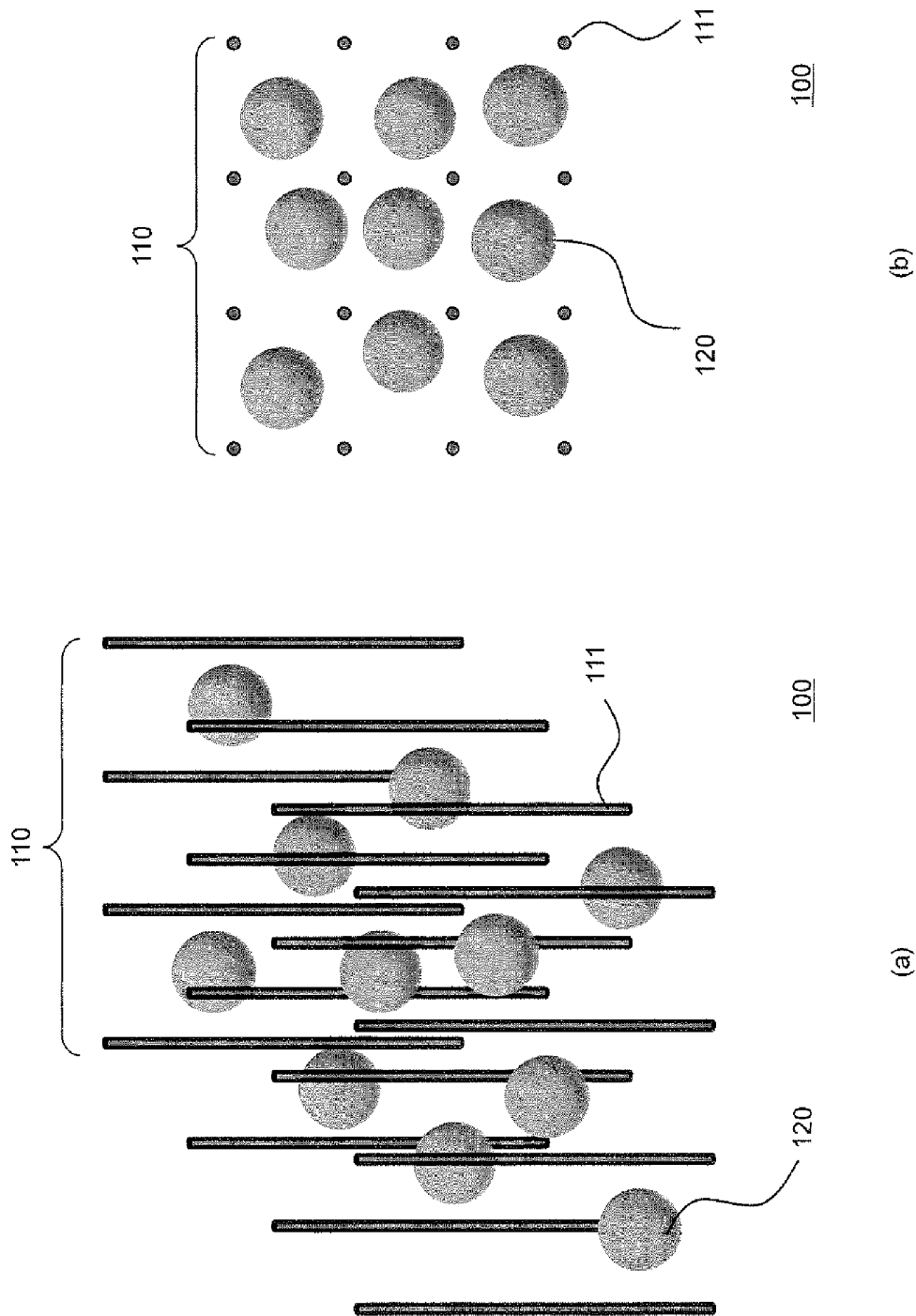
FIG. 1 is an exemplary view of a carbon nanotube film 100 related to one embodiment of the present invention, (a) is a perspective view and (b) is an upper surface view.

An exemplary view of a carbon nanotube film 100 related to an embodiment of the present invention is shown in FIG. 1. The carbon nanotube film 100 includes a structure in which a carbon nanotube aggregate 110 aggregated with a CNT 111 contains a protein 120. In other words, the protein 120 exists among CNT 111 which forms the carbon nanotube aggregate 110 aggregated with the CNT 111. A protein (enzyme) which includes redox activity is used as the protein 120. However, an inactive protein or a protein which does not obstruct a reaction of a protein which includes redox activity may also be included.

It is preferred that an orientated single-walled CNT is used as the CNT 111 which forms the carbon nanotube aggregate 110 related to the present embodiment. The CNT 111 can be synthesized using the super growth method mentioned above. It is possible to obtain the carbon nanotube aggregate 110 by peeling an aggregate of the synthesized CNT 111 from a synthetic substrate.

The relative surface area of the carbon nanotube aggregate 110 used in the carbon nanotube film 100 is preferred to be 600 $m^2/g$ or more and 1,300 $m^2/g$ or less if unopened single-walled CNTs are mainly present. The relative surface area of the carbon nanotube aggregate 110 used in the carbon nanotube film 100 is preferred to be 1,300 $m^2/g$ or more and 2,600 $m^2/g$ or less if opened single-walled CNTs are mainly present. It is possible to calculate the relative surface area of a carbon nanotube aggregate by measuring an absorption/desorption isotherm curve at 77K of liquid nitrogen. Sheet resistance of the carbon nanotube aggregate 110 is 1.74 $\Omega/cm^2$ or more in a perpendicular direction and 2.61 $\Omega/cm^2$ or more in a parallel direction. In addition, weight density of the carbon nanotube aggregate 110 is 0.002 $g/cm^3$ or more and 0.2 $g/cm^3$ or less.

In the present embodiment, the carbon nanotube aggregate 110 used in the carbon nanotube film 100, for example, as typical values, has a single-walled CNT contained ratio of 98% or more (ratio of the number of single-walled CNTs with respect to double layer CNTs and multi-layer CNTs calculated from a transmission type electron microscope image of the carbon nanotube aggregate), a pore size distribution maximum of 5 nm or more and 100 nm or less, metal impurities of 0.01 mass % or less, a carbon purity of 99.9 mass % or more, a G/D ratio of 50 or less, an average external diameter of 1.5 nm or more and 4 nm or less, a half value width of 1 nm, and a Herman orientation factor of 0.1 or more and 1 or less.

It is preferred that the enzyme 120 used in the carbon nanotube film 100 related to the present embodiment is an oxidase such as dehydrogenase, or for example, a combination of diaphorase and glucose dehydrogenase, or selected from enzymes such as glucose oxidase, fructose oxidase, fructose dehydrogenase, alcohol oxidase, alcohol dehydrogenase, lactate oxidase or lactate dehydrogenase as the enzyme included in an anode electrode. The enzyme which can be used in the anode electrode is not limited to these. For example, any enzyme can be used as long as the enzyme is useful in the degradation of a biomass fuel such as sugar or alcohol.

In addition, it is preferred that an enzyme with oxygen such as oxidase as the substrate, for example, an enzyme such as a multicopper oxidase such as bilirubin oxidase or laccase is used as the enzyme included in an cathode electrode. However, the enzyme which can be used in the cathode electrode is not limited to these. For example, any enzyme can be used as it is useful in oxidation-reduction.

(Manufacturing Method of a Carbon Nanotube Film)

The manufacturing method of a carbon nanotube film described above is explained below. The carbon nanotube film is manufactured by including the enzyme 120 in the carbon nanotube aggregate 110. Because the carbon nanotube aggregate 110 contains a very high level of hydrophoby, including the enzyme 120 in the carbon nanotube aggregate 110 is not easy. The inventors of the present invention discovered a method for including an enzyme in the carbon nanotube aggregate 110 after repeated trial and error. Specifically, since a biomolecule has a fragile structure it is necessary to consider the mildness of a process in an inclusion and contraction process. This means that it is impossible to realize this if the materials used in the constriction process of the free-standing film proposed in the present application and the conditions are not together. There are two methods that can be used as an inclusion method, a method of immersing a carbon nanotube aggregate in a static enzyme solution and a method of immersing a carbon nanotube aggregate in a stirred enzyme solution. In addition, it is possible to reduce the size of the carbon nanotube film 100 by constricting the carbon nanotube aggregate by drying after including the enzyme 120 in the carbon nanotube aggregate 110. The carbon nanotube film before construction is called "as grown" and the carbon nanotube film after constriction is called "solid" below.

(Peeling Process)

Figure 3:
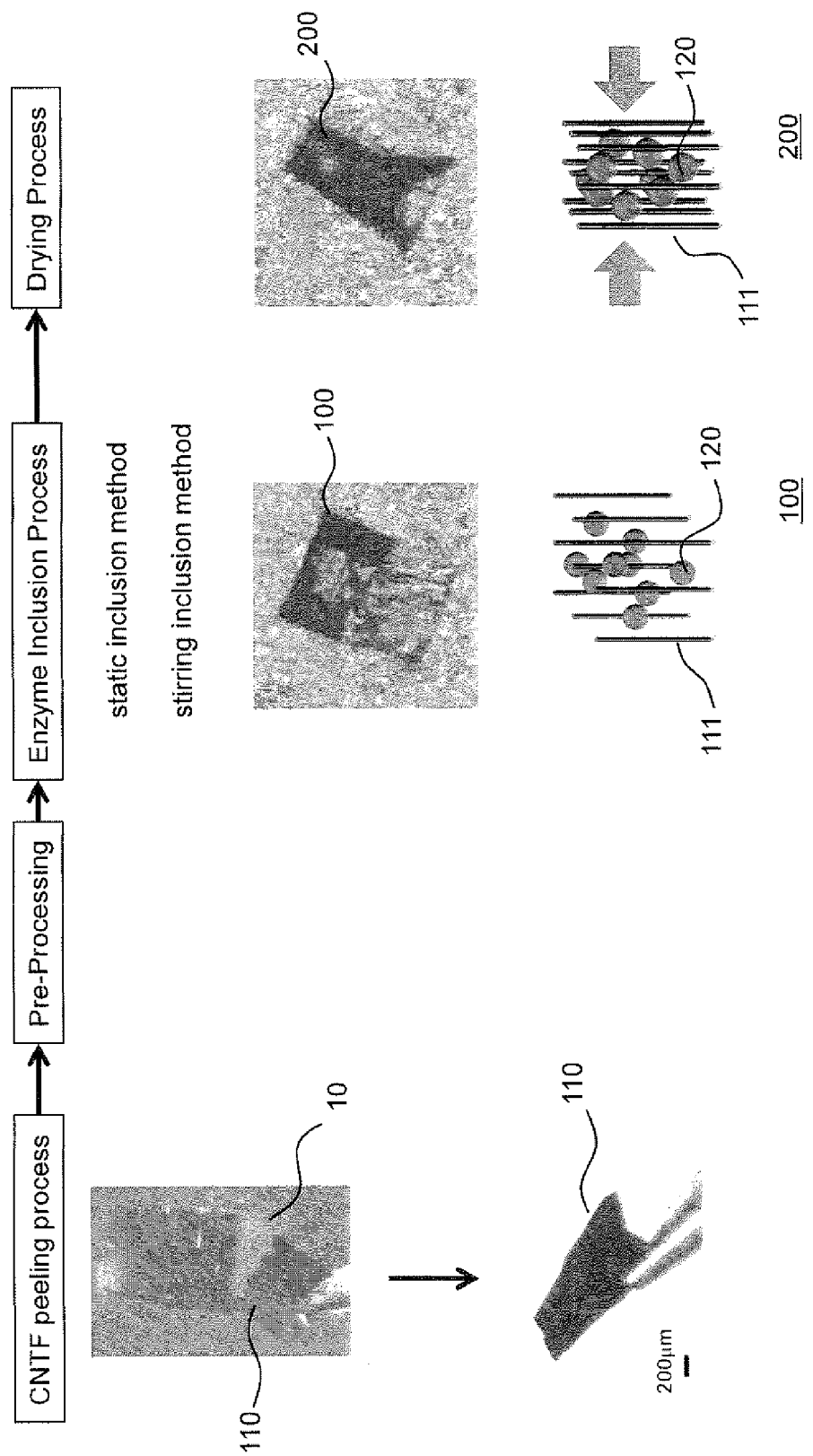
FIG. 3 shows a manufacturing method of a carbon nanotube film related to one embodiment of the present invention.

FIG. 3 shows a manufacturing method of the carbon nanotube film 100 related to the present embodiment. The carbon nanotube aggregate related to the present embodiment can be manufactured using the supper growth method (International Published Patent WO2006/011655) reported by the inventors. A manufacturing process of the carbon nanotube film 100 can include a carbon nanotube aggregate peeling process, pre-processing and an enzyme inclusion process, and a drying process additionally. The carbon nanotube aggregate peeling process is a process of peeling a sheet shaped carbon nanotube aggregate 110 from a highly orientated CNT aggregate synthesized on a synthetic substrate. Even if the carbon nanotube aggregate is peeling, catalyst particles formed on a synthetic substrate for synthesizing the carbon nanotube aggregate 110 are almost never peeled from the top of the synthetic substrate. As a result, in the carbon nanotube aggregate peeling process it is possible to obtain a highly pure carbon nanotube aggregate 110 without including hardly any catalyst particles in the carbon nanotube aggregate 110.

(Pre-Processing)

The pre-processing process is for immersing the peeled carbon nanotube aggregate 110 in a buffer solution for a certain period of time under reduced pressure conditions. By reducing pressure, any gas remaining within the carbon nanotube aggregate 110 is deaerated. The carbon nanotube aggregate 110 is sufficiently deaerated in order to easily immerse a solution which includes the enzyme 120 in the carbon nanotube aggregate 110 in the next enzyme inclusion process. It was discovered that it is possible to realize sufficiently including an enzyme into a carbon nanotube aggregate via this deaeration process. A surfactant may also be added to the buffer solution. In addition, an ionic liquid may be used instead of a surfactant. Because a CNT is hydrophobic it is possible to increase the affinity to water by adding a surfactant. In addition, the carbon nanotube aggregate 110 forms a free-standing type carbon nanotube film by immersing a water component among the CNT 111.

TritonX-100, Tween 20 etc or any surfactant that does not affect the activity of the enzyme 120 can be used as the surfactant used in the pre-processing process of the carbon nanotube aggregate 110 related to the present embodiment. In addition, any buffer solution may be used as the buffer solution as long as it does not affect the activity of the enzyme 120 such as phosphate buffered saline, PBS, or McIlvaine buffer solution.

(Enzyme Inclusion Process)

Next, the enzyme 120 is included in the carbon nanotube aggregate 110 using an enzyme inclusion process. In the enzyme inclusion process the carbon nanotube aggregate 110 is immersed in an enzyme solution for a certain period of time. Following this, the carbon nanotube aggregate 110 containing the enzyme 110 is washed using a buffer solution and the carbon nanotube film 100 (as grown) is obtained. Here, the enzyme inclusion process can be performed using a static inclusion method or a stirring inclusion method.

The static inclusion method is a method for including the enzyme 120 by leaving the carbon nanotube aggregate 110 to stand for a certain period of time within the enzyme solution. In addition, the stirring inclusion method is a method for including the enzyme 120 by immersing the carbon nanotube aggregate 110 for a certain period of time in a stirred enzyme solution. While it is possible to use either the static inclusion method of the stirring inclusion method in the enzyme inclusion process, as is shown in the examples described below, the stirring inclusion method can include the enzyme 120 in the carbon nanotube aggregate 110 more efficiently compared to the static inclusion method. In addition, in the enzyme inclusion process, it is possible to adjust the amount of included enzyme in a carbon nanotube aggregate by changing the concentration of the enzyme solution.

(Drying Process)

Figure 2:
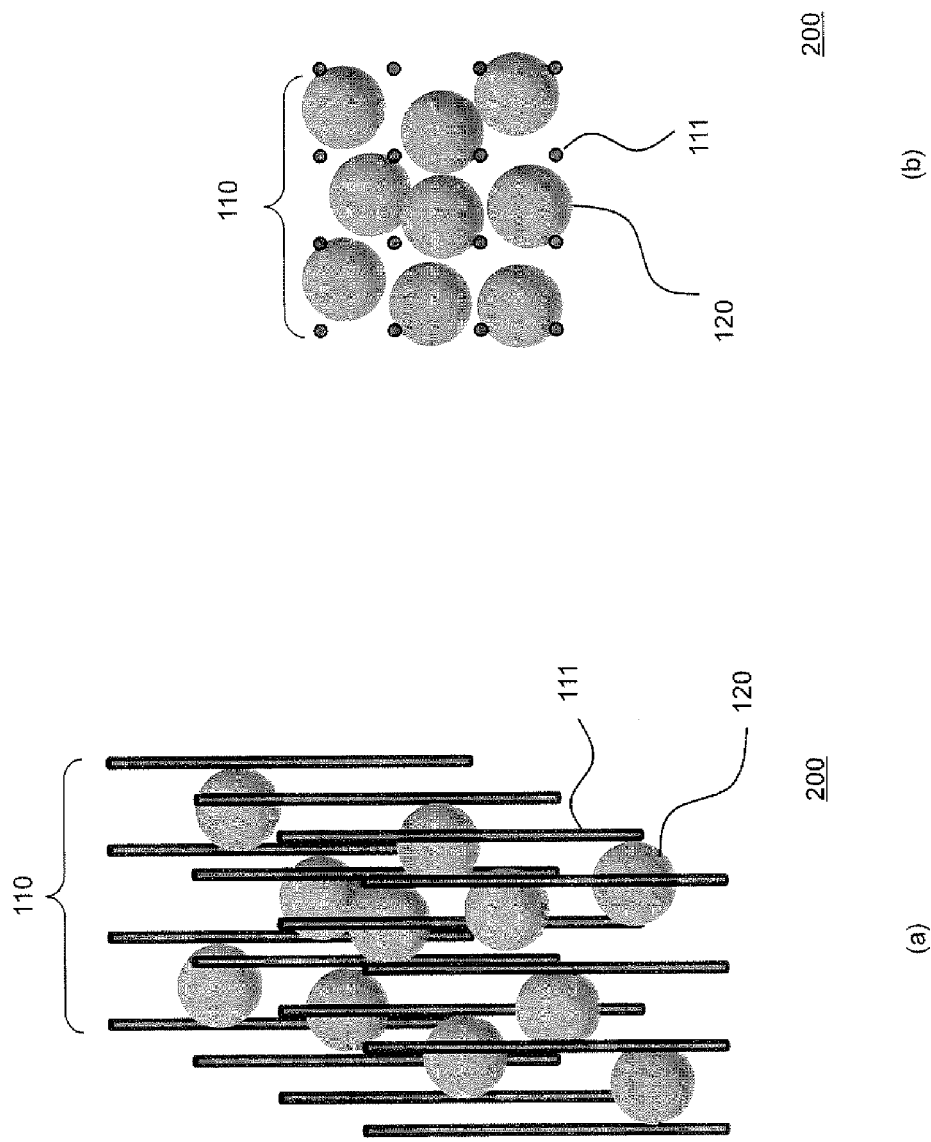
FIG. 2 is an exemplary view of a carbon nanotube film 200 related to one embodiment of the present invention, (a) is a perspective view and (b) is an upper surface view.

The carbon nanotube film 100 containing the enzyme 100 may further be dried by a drying process. When the carbon nanotube film 100 is dried in an atmosphere under room temperature on carbon paper (abbreviated to CP herein), the carbon nanotube film 100 constricts. By drying the carbon nanotube film 100 it is possible to produce a small scale free standing type film. In addition, as is shown in FIG. 2, when the carbon nanotube film 100 constricts due to drying, the intervals among the CNT 111 become narrower to the extent of the contained enzyme 120. In this way, as is shown in FIG. 2, it is possible to provide a carbon nanotube film 200 (solid) with a high reaction density by efficiently contacting the CNT 111 and enzyme 120.

In addition, while the size of the intervals among the CNT 111 become the extent of the contained enzyme 120 when the carbon nanotube film 200 constricts due to drying, it is also possible to simultaneously include a different type of protein with different sized molecules to the enzyme 120. For example, in the case of including a protein which is larger than the enzyme 120 and does not obstruct inactivity or an enzyme reaction of the enzyme 120, it is possible to provide a place for a reaction in order to improve the reaction efficiency of the enzyme 120 within the carbon nanotube film 200.

In the present embodiment, a mediator may further be included in the carbon nanotube film. A known mediator may be used as the mediator.

(Attachment to a Flexible Substrate)

Because the carbon nanotube films 100, 200 manufactured as described above include flexibility it is possible to use the films when attached to a flexible substrate. FIG. 4 shows an example where a carbon nanotube film is attached to a flexible substrate 150. For example it is possible to use Polyethylene Terephthalate (PET) or a collagen gel as the flexible substrate 150 related to the present invention. After the enzyme 120 is included using the enzyme inclusion method described above, the carbon nanotube film 100 is placed on the flexible substrate 150 and dried under an atmosphere at room temperature. In addition, in the case where the carbon nanotube film 200 is attached to the flexible substrate 150, the carbon nanotube film is moistened using the buffer solution described above and attached to the flexible substrate 150. After a carbon nanotube film is attached to a base material such as the substrate 150, the film is maintained in a state where the protein 120 is included without widening the intervals within the CNT 111 even when immersed in a solution.

As is shown in FIG. 4, even in a state where the flexible substrate 150 is curved, the carbon nanotube film 200 curves with the flexible substrate 150 but does not peel. Because the substrate includes a property which absorbs a fuel solution when forming a power generating device especially when a collagen gel is used as the flexible substrate 150, it is possible to prepare a fuel integrated type small biofuel cell.

As explained above, by including an enzyme in a high orientation carbon nanotube aggregate with excellent electrical conductivity, the carbon nanotube film of the present invention related to the present embodiment can efficiently accept electrons with an redox protein and free standing film with flexibility is provided. In addition, the size of the protein included in the CNT intervals is adjusted by drying the carbon nanotube film related to the present embodiment, the film is small with high reaction density and functions as an electrode which physically maintains an enzyme, activity and has excellent electron transfer efficiency. Furthermore, because the carbon nanotube film related to the present embodiment is provided with both mechanical strength and flexibility, it is possible to prepare a flexible biosensor or power generating device formed only with a clean organic material.

Second Embodiment (Power Generating Device)

Figure 5:
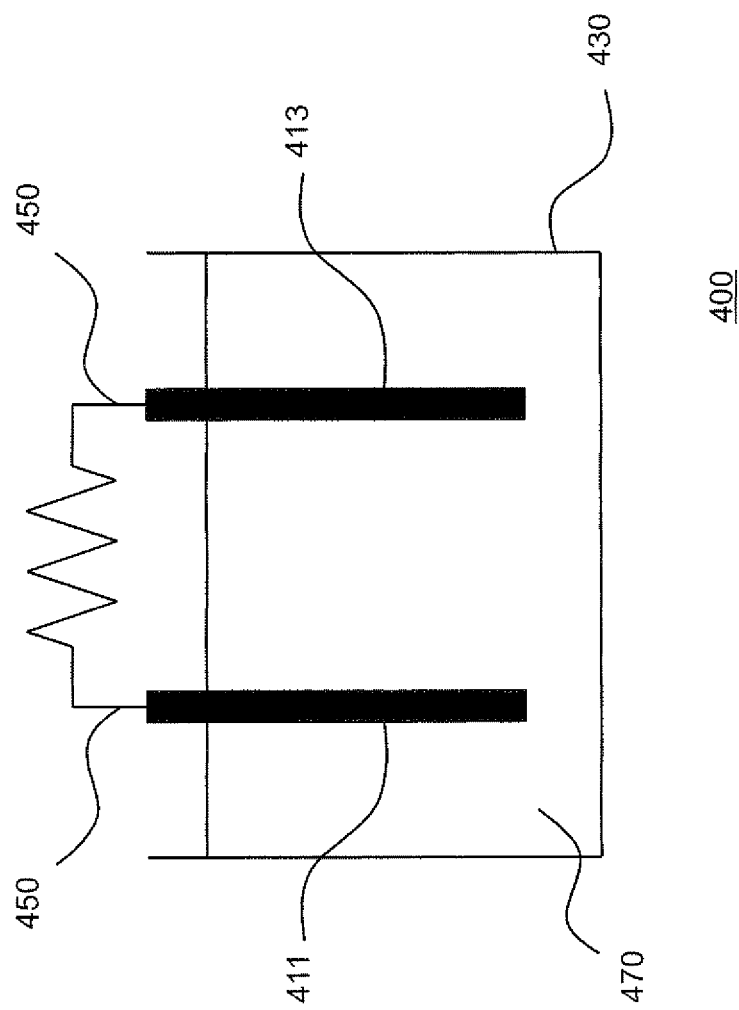
FIG. 5 is an exemplary view of a power generating device 400 related to one embodiment of the present invention.

In the present embodiment a power generating device 400 is explained using the carbon nanotube film explained in the first embodiment. FIG. 5 is an exemplary view of the power generating device 400 related to the present embodiment of the present invention. The power generating device 400 has a structure in which an anode electrode 411 and cathode electrode 413 are arranged at certain intervals on the interior side of a container 430 and is filled with fuel 470. Wiring 450 is connected to the anode electrode 411 and cathode electrode 413 and electrical energy is extracted from the power generating device 400. The container 430 and wiring 450 can each be formed using a known material.

In addition, it is preferred that the fuel 470 of the power generating device 400 related to the present embodiment is selected from grape sugar (glucose), fruit sugar (fructose), alcohol such as methanol or ethanol, lactic acid or sucrose. The fuel which can be used is not limited to these however, anything can be used as long as it can be used as the substrate of the anode electrode enzyme and cathode electrode enzyme explained in the first embodiment.

Figure 6:
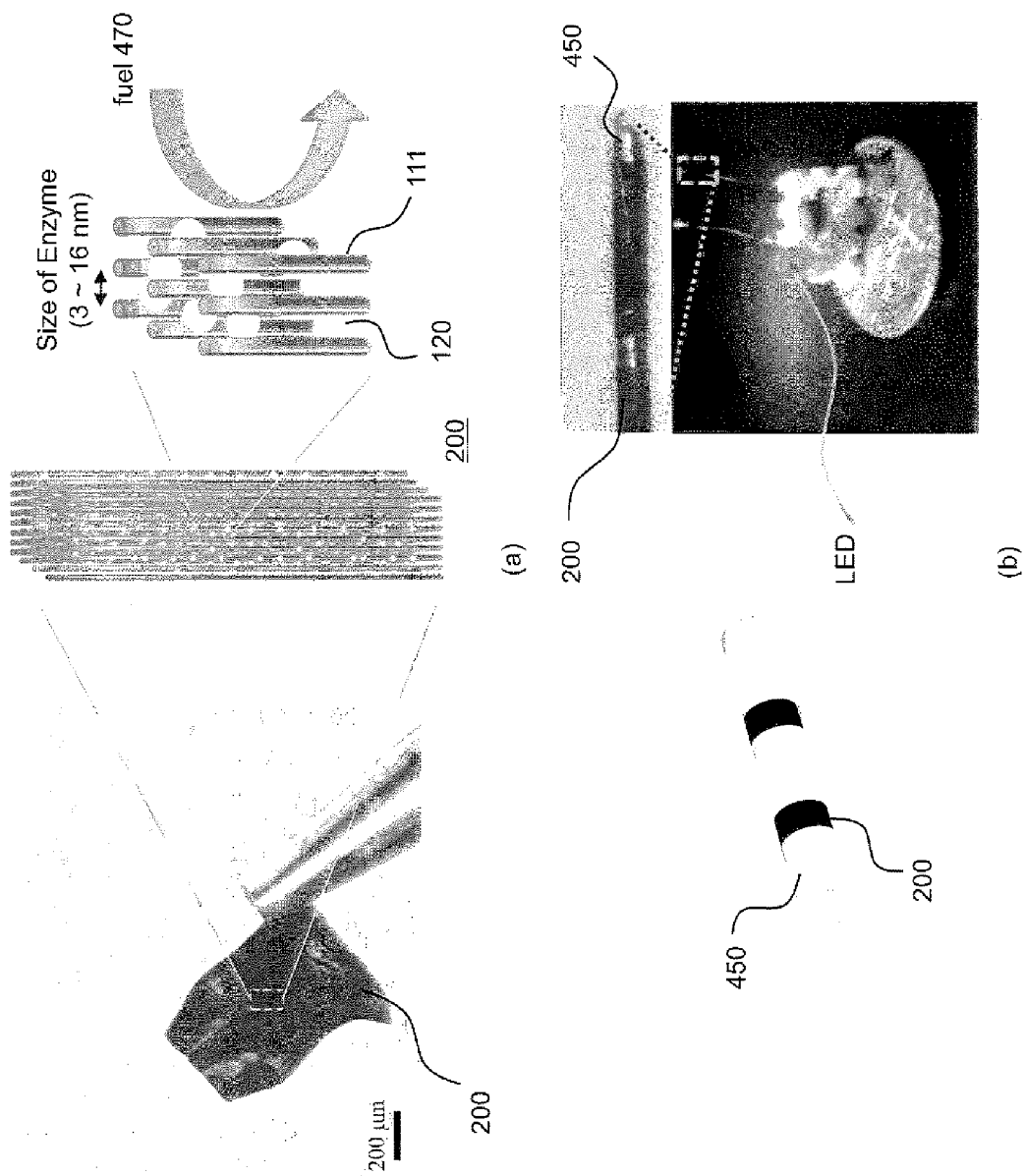
FIG. 6 shows an electrode of the power generating device 400 related to one embodiment of the present invention, (a) shows an optical photograph and an exemplary view of the carbon nanotube film 100 and (b) is an exemplary view and optical photograph of the electrode.

The anode electrode 411 and the cathode electrode 413 can be formed for example by winding the wiring 450 around the carbon nanotube film 100. FIG. 6 shows an electrode of the power generating device 400 shown in FIG. 5 related to the present embodiment. As is shown in FIG. 6 (a), in the power generating device 400, the fuel 470 is immersed in a carbon nanotube film and the included enzyme 120 generates electrical energy with the fuel 470 as a substrate. As is shown in FIG. 6 (b), because the carbon nanotube film includes flexibility it is possible to wind the film on the wiring 450 and the film functions as an electrode in the power generating device 400.

The anode electrode 411 and the cathode electrode 413 can be formed by winding the carbon nanotube film 100 on the wiring 450 and drying in an atmosphere under room temperature. It is possible to use the carbon nanotube film 100 and carbon nanotube film 200 explained in the first embodiment as the carbon nanotube film used in the electrode of the power generating device 400 of the present embodiment. In the case where the carbon nanotube film 100 is used, the film may be wound on the wiring 450. However, in the case where the carbon nanotube film 200 is used, the carbon nanotube film is moistened using the buffer solution described above and wound on the wiring 450. After the carbon nanotube film is attached to a base material such as the wiring 450, the film is maintained in a state where the protein 120 is included without widening the intervals within the CNT 111 even when immersed in a solution.

As explained above, in the power generating device of the present invention related to the present embodiment, it is possible to form a flexible, free standing film used in an electrode, in which an enzyme is included in a high orientation carbon nanotube aggregate with excellent electrical conductivity. Because the carbon nanotube film related to the present embodiment is provided with both mechanical strength and flexibility, it is possible attach or wind the film to a substrate material or wiring and provide a flexible power generating device formed only with a safe and clean organic material Third Embodiment (Biosensor)

The carbon nanotube film off the present invention explained in the first embodiment can obtain electrical energy using an oxidation-reduction reaction of a fuel as explained in the second embodiment. Similarly, the carbon nanotube film of the present invention can be applied to a biosensor which detects a substance to be tested by detecting an oxidation-reduction current.

Specifically, it is possible to detect grape sugar (glucose), fruit sugar (fructose), ethanol, lactic acid or sucrose etc which are to be analyzed in health monitoring or food product analysis etc. The substance to be measured is not limited to these however and can be any substance which becomes the substrate of an included enzyme.

It is possible to use the carbon nanotube film attached to the flexible substrate explained in the first embodiment or electrode explained in the second embodiment in the biosensor related to the present embodiment. In addition, it is also possible to use either the carbon nanotube film 100 or carbon nanotube film 200 in the biosensor related to the present embodiment.

As explained above, in the biosensor of the present invention related to the present embodiment, it is possible to form a flexible, free standing film used in a sensor, in which an enzyme is included in a high orientation carbon nanotube aggregate with excellent electrical conductivity. Because the carbon nanotube film related to the present embodiment is provided with both mechanical strength and flexibility, it is possible attach or wind the film to a substrate material or wiring and provide a flexible biosensor formed only with a safe and clean organic material An example of a carbon nanotube film, and a sensor and power generating device each equipped with the carbon nanotube film as an electrode related to the invention of the present embodiment described above is explained in detail below. Furthermore, the examples explained below are just examples and the carbon nanotube film, and a sensor and power generating device each equipped with the carbon nanotube film as an electrode of the present invention is not limited to these examples.

(Manufacture of a Carbon Nanotube Film)

An example of a method of manufacturing the carbon nanotube film 100 is shown below.

The CNT 111 which forms the carbon nanotube aggregate 110 related to the present example is synthesized using the super growth method described above. An aggregate of the synthesized CNT 111 is peeled from a silicon substrate using tweezers and the carbon nanotube aggregate 110 is obtained.

Using the carbon nanotube aggregate 110 with mainly unopened CNTs, the carbon nanotube film 100 included a CNT 111 length of 1 mm, CNT 111 interval of 16 nm, sheet resistance of 1.74 $\Omega/cm^2$ or more in a perpendicular direction and 2.61 $\Omega/cm^2$ or more in a parallel direction and other characteristics were in the range shown in the first embodiment described above.

(Enzyme Inclusion Using a Static Inclusion Method)

The carbon nanotube aggregate 110 peeled from the silicon substrate is held between reverse type tweezers. The carbon nanotube aggregate is immersed in a buffer solution containing 1% of a surfactant (Triton X-100) and deaerated for 30 minutes in a vacuum chamber (~1 MPa). It is possible to sufficiently include an enzyme in the carbon nanotube aggregate via this deaeration process. Next, the aggregate anchored with tweezers is immersed in 1 ml of an enzyme solution (anode: D-fructose Dehydrogenese 10 mg/ml, cathode: Laccase 4.3 µM, McIlvaine Buffer (pH 5.0) is used for the buffer solution). Following this the carbon nanotube aggregate is cleaned by blotting with a pipette and pouring out into 10 ml of the McIlvaine Buffer. In this way, the carbon nanotube 100 (as grown) is obtained.

(Enzyme Inclusion Using a Stirring Inclusion Method)

The carbon nanotube aggregate 110 peeled from the silicon substrate is held between reverse type tweezers. The carbon nanotube aggregate is immersed in a buffer solution containing 1% of a surfactant agent (Triton X-100) and deaerated for 30 minutes in a vacuum chamber (~1 MPa). It is possible to sufficiently include an enzyme in the carbon nanotube aggregate via this deaeration process. Next, the carbon nanotube aggregate held by the tweezers is immersed in a vial containing 1 ml of an enzyme solution (anode: D-fructose Dehydrogenese 0.5 mg/ml, cathode: Laccase 4.3 µM, McIlvaine Buffer (pH 5.0) is used for the buffer solution) and a stirrer so that the aggregate does not interfere with the stirrer. Following this, the carbon nanotube aggregate is immersed for 12 hours while stirring the solution at 4° C. After the carbon nanotube aggregate is released from the tweezers into the solution, the carbon nanotube aggregate within the solution was blotted using a pipette. Following this, the carbon nanotube aggregate was cleaned by pouring out into 10 ml of the buffer solution (McIlvaine Buffer (pH 5.0)).

(Drying the Carbon Nanotube Aggregate)

Figure 7:
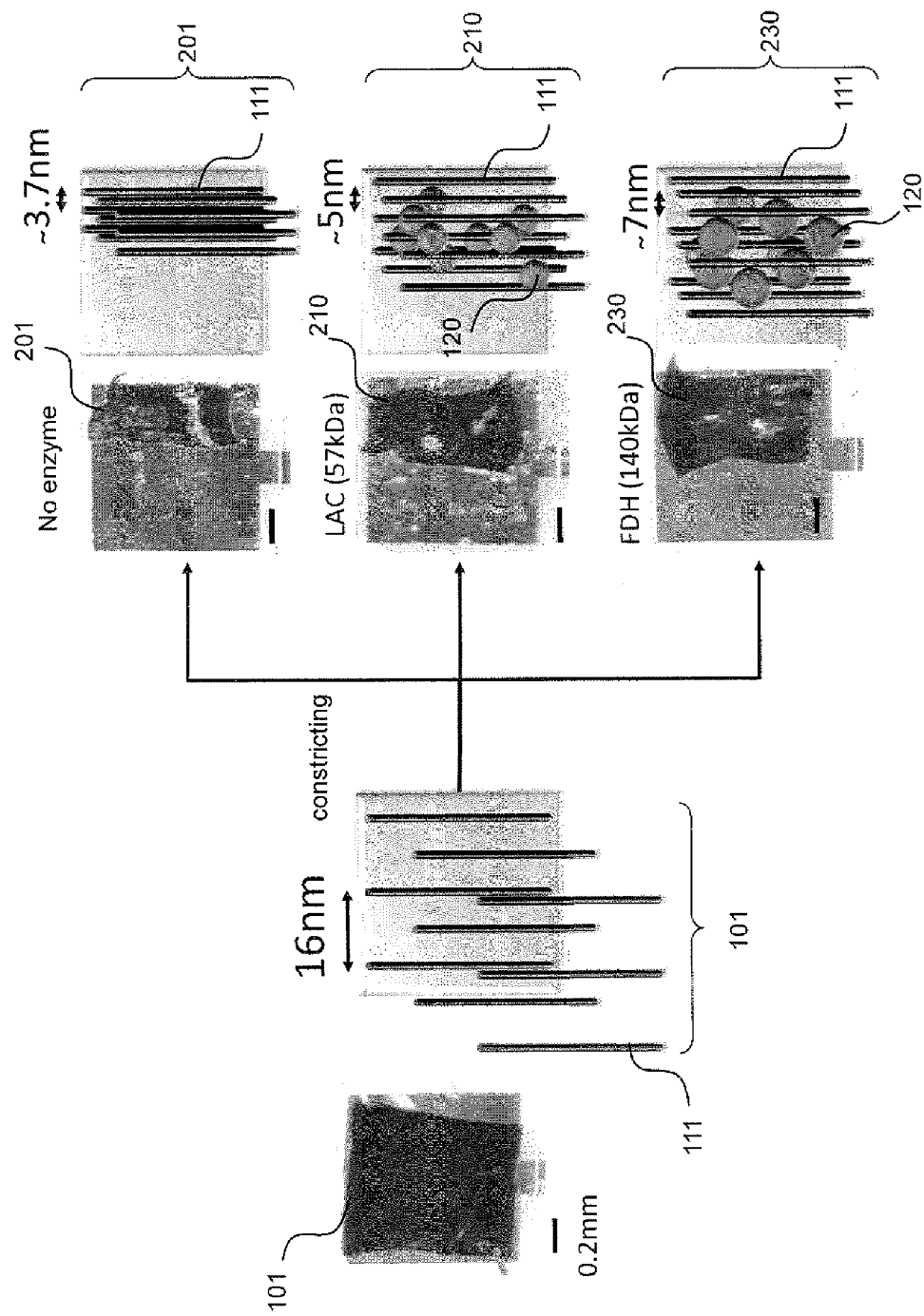
FIG. 7 shows the relationship between the size of a contained enzyme and the size of the carbon nanotube film 100 after drying related to one example of the present invention.

After the carbon nanotube aggregate is cleaned, it is poured onto carbon paper (abbreviated to CP below) and constricted by drying in an atmosphere at room temperature. The carbon nanotube film constricted by the drying process was observed using an optical microscope. In the present example, using the carbon nanotube aggregate 110 with CNT 111 intervals of 16 nm, a carbon nanotube film 201 with only a buffer solution which does not contain the enzyme 120, a carbon nanotube film 210 containing Laccase (LAC) as the enzyme 120 and a carbon nanotube film 230 containing D-fructose Dehydrogenese (FDH) as the enzyme 120 were each constricted by the drying process and the carbon nanotube film 200 (solid) was obtained. As is shown in FIG. 7, it can be seen that the constriction rate of the carbon nanotube film changes depending on the size of the contained enzyme.

(Evaluation of the Conduction Capabilities of a Carbon Nanotube Film)

The evaluation results of the conduction capabilities of a carbon nanotube film are shown below. The evaluation of the conduction capabilities of a carbon nanotube film was performed using an anode which oxidizes a fuel and a cathode which reduces an enzyme. The capacitance of the carbon nanotube aggregate was evaluated in order to estimate the permitted amount of an enzyme which can be included.

The carbon nanotube film 101 (as grown) which is not constricted is used as the first example and the carbon nanotube film 201 (solid) which is constricted is used as the second example. In addition, a non-orientated CNT is used as an electrode as a comparative example, a non-orientated CNT 910 with a length of 1 mm is used in comparative example 1, and a non-orientated CNT 920 with a length of 2~5 μm is used in comparative example 2. Example 1, example 2, comparative example 1 and comparative example 2 are each prepared as follows.

(Evaluation of the Capacitance Volume of a Carbon Nanotube Film)

An electrode was prepared for measuring the capacitance of the carbon nanotube film 101 and the carbon nanotube film 201. A carbon nanotube aggregate extending n a perpendicular direction from a silicon substrate was peeled using tweezers and immersed in DMF (N, N-dimenthylformide, manufactured by Sigma). The carbon nanotube aggregate was blotted with a pipette, placed on a gold electrode (electrode area of 0.01 cm$^2$) prepared on a glass substrate and the carbon nanotube aggregate (as grown) was prepared by drying in an atmosphere at room temperature. After the carbon nanotube aggregate (solid) was immersed in the DMF, the aggregate was poured on carbon paper, constricted by drying in an atmosphere at room temperature and placed on a gold electrode (electrode area of 0.01 cm$^2$) using tweezers. The DMF was dripped and dried in an atmosphere at room temperature. A CNT (length: 1 mm) which disperses the carbon nanotube aggregate using an ultrasonic homogenizer and a CNT (length: 2~5 μm) which similarly disperses a commercially available CNT was used as the non-orientated CNT. DMF was used to prepare the electrode and 90 ng/μl of a CNT solution was prepared. The CNT solution was subjected to ultrasound for 15 minutes at 10 W using an ultrasonic homogenizer (Sonifier 250D BRANSON) and the CNT was dispersed. 2.6 μl of the dispersed solution was dripped onto the gold electrode and dried for 1.5 hours in a vacuum oven at 80° C. These electrodes were observed using an electron microscope (FIG. 8 (a)).

The capacitance volume was calculated by measuring impedance Z and frequency f using a current impedance method, and inserting into the formula (1).

$$C=1/(2\pi fz) \quad (1)$$

An electrochemical measurement system (Electrochemical Analyzer Model 600S, manufactured by BAS) was used as the measuring instrument and an alternating electric field of ±5 mV and a frequency of 1 Hz~1×10$^5$ Hz in a buffer solution (McIlvaine Buffer (pH 5.0)) were used as the measurement conditions. Capacitance volume using alternating current impedance is shown in FIG. 8 (b). It can be seen that a volume of the film of the carbon nanotube aggregate in example 1 and example 2 was more than twice compared to the non-orientated CNT in comparative example 1 and comparative example 2. In addition, it can be seen that there was no significant difference in the capacitance volume of the carbon nanotube aggregate before or after constriction.

(Evaluation of Anode Electrode Capabilities)

Next, an anode electrode was prepared and its capabilities were evaluated. A film 510 of a carbon nanotube aggregate which is not constricted using a static inclusion method was prepared as example 3, a carbon nanotube film 520 which is not constricted using a stirring inclusion method was prepared as example 4, and a carbon nanotube film 530 which is constricted using a stirring inclusion method was prepared as example 5. In addition, a 1 mm long non-orientated CNT 910 was used as comparative example 3 and a 2~5 μm long non-orientated CNT 920 was used as comparative example 4.

Figure 9:
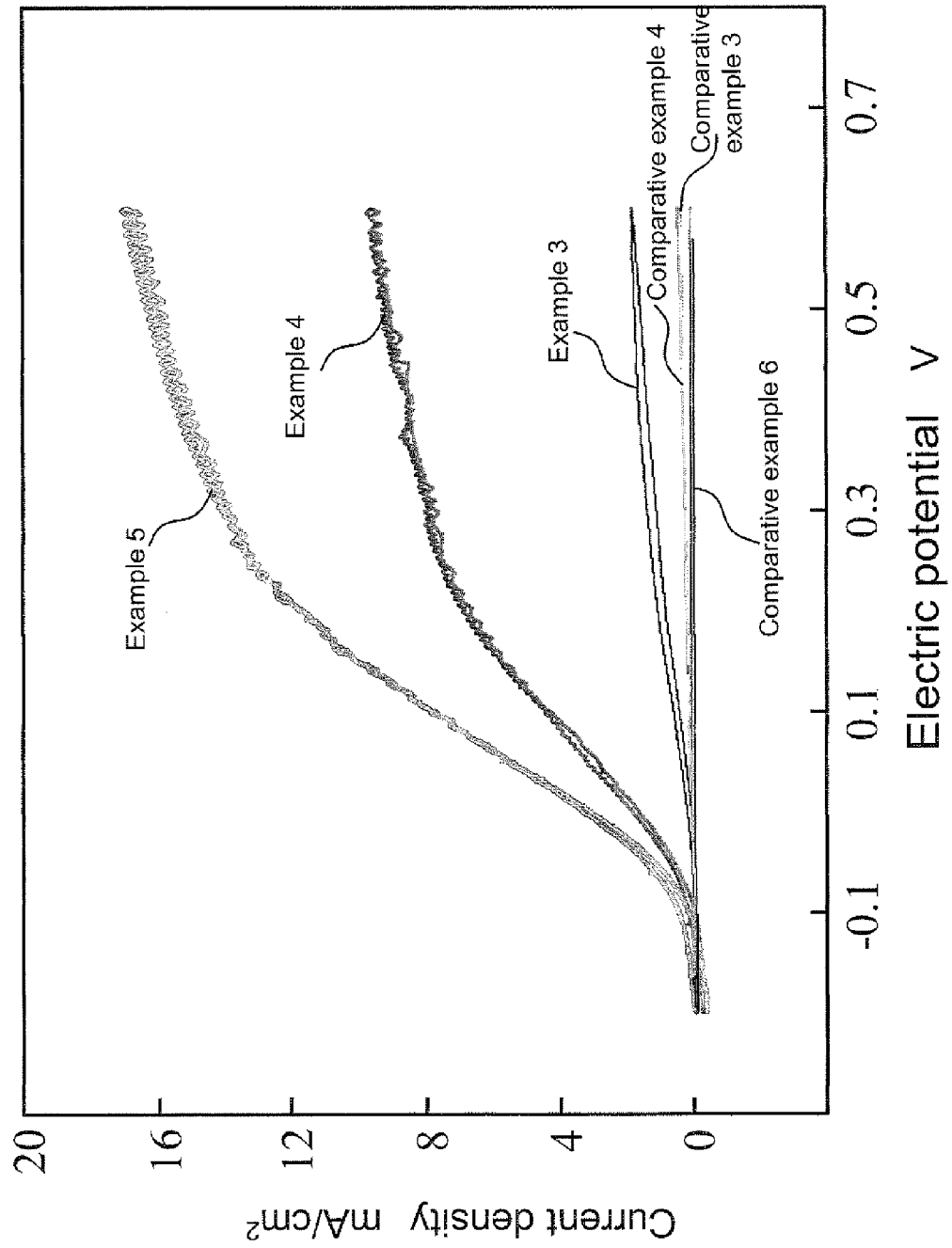
FIG. 9 shows a current, potential curve of fructose oxidation by an anode electrode in the examples and comparative examples.

After the anode electrode was prepared using a carbon nanotube film, the film was placed on a gold electrode (electrode area of 0.01 cm$^2$) and a buffer solution was dripped onto the electrode. After drying the film was attached to the electrode and a carbon nanotube film electrode was prepared. An enzyme was incorporated into the non-orientated CNT electrode in the comparative examples by dripping an enzyme solution (D-fructose Dehydrogenese 10 mg/ml) on the electrode prepared by the method explained in the evaluation of capacitance volume. A current, potential curve of fructose oxidation is shown in FIG. 9. The current, potential curve was obtained by a three electrode method (working: enzyme electrode, reference: Ag/AgCl sat. KCl, counter: platinum) using an electrochemical measurement system (Electrochemical Analyzer Model 600S, manufactured by BAS). The measurement conditions were a sweep velocity of 10 mV/s at room temperature in 200 mM of a fructose solution.

The non-orientated CNTs in comparative example 3 and comparative example 4 had about the same current density. However, the carbon nanotube film 510 which is not constricted using the static inclusion method in example 3 showed a significantly larger current density compared to the comparative examples. In addition, the carbon nanotube film 520 which is not constricted using the stirring inclusion method in example 4 showed about 20 times the current density compared to the comparative examples and the carbon nanotube film 530 which is constricted using the stirring inclusion method in example 5 showed an excellent current density of about 40 times compared to the comparative examples. Although example 4 and example 5 show a maximum current of about the same value, the current density was the largest in example 5 given the amount of constriction. This suggests that no drop in enzyme activity due to constriction of a carbon nanotube film is observed.

(Evaluation of Cathode Electrode Capabilities)

Similarly, a cathode electrode was prepared and its capabilities were evaluated. A carbon nanotube film 510 which is not constricted using a static inclusion method was prepared as example 7, a carbon nanotube film 520 which is not constricted using a stirring inclusion method was prepared as example 8, and a carbon nanotube film 530 which is constricted using a stirring inclusion method was prepared as example 9. In addition, a 1 mm long non-orientated CNT 910 was used as comparative example 5 and a 2~5 μm long non-orientated CNT 920 was used as comparative example 6.

Figure 10:
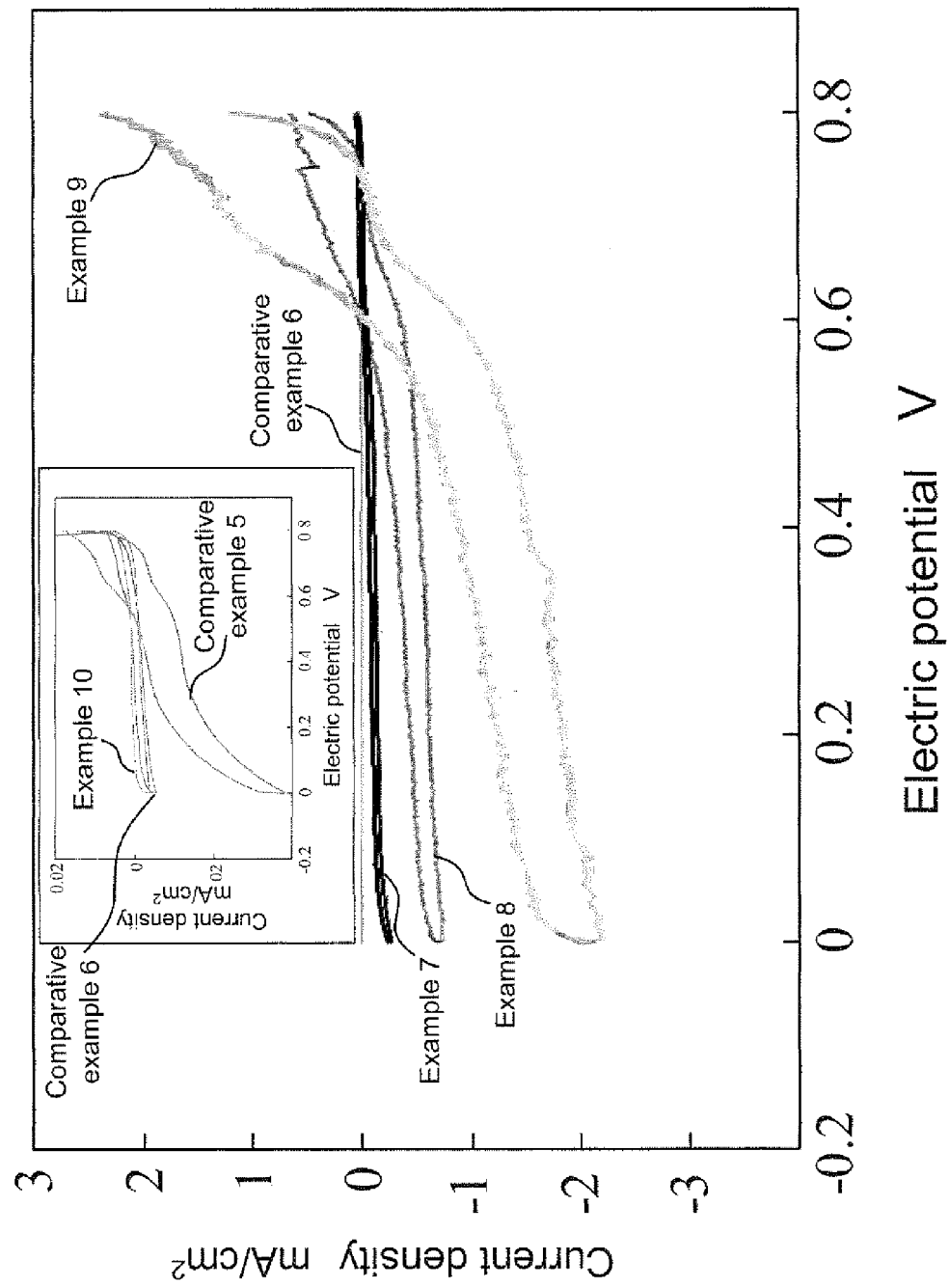
FIG. 10 shows a current, potential curve of oxygen reduction by a cathode electrode in the examples and comparative examples.

The same method used for preparing the anode electrode described above was used as the preparation method of each electrode. An enzyme reduction current, potential curve is shown in FIG. 10. The current, potential curve was obtained using a device which is used in the evaluation of the anode electrode capabilities, under the same conditions and under enzyme neutral conditions.

The current, potential curve was the same as the result obtained in the evaluation of the anode electrode capabilities and the non-orientated CNT in comparative example 5 and comparative example 6 had about the same current density. However, the carbon nanotube film 510 which is not constricted using the static inclusion method in example 7 showed a significantly larger current density compared to the comparative examples. In addition, the carbon nanotube film 520 which is not constricted using the stirring inclusion method in example 8 showed about 20 times the current density compared to the comparative examples and the carbon nanotube film 530 which is constricted using the stirring inclusion method in example 9 showed an excellent current density of about 60 times compared to the comparative examples. Although example 8 and example 9 show a maximum current of about the same value, the current density was the largest in example 9 given the amount of constriction. This suggests that no drop in enzyme activity due to constriction of a carbon nanotube film is observed.

(Preparation of a Sensor and Power Generating Device and Capabilities Evaluation)
(Output Evaluation of a Bio-Power Generating Device)

Figure 11:
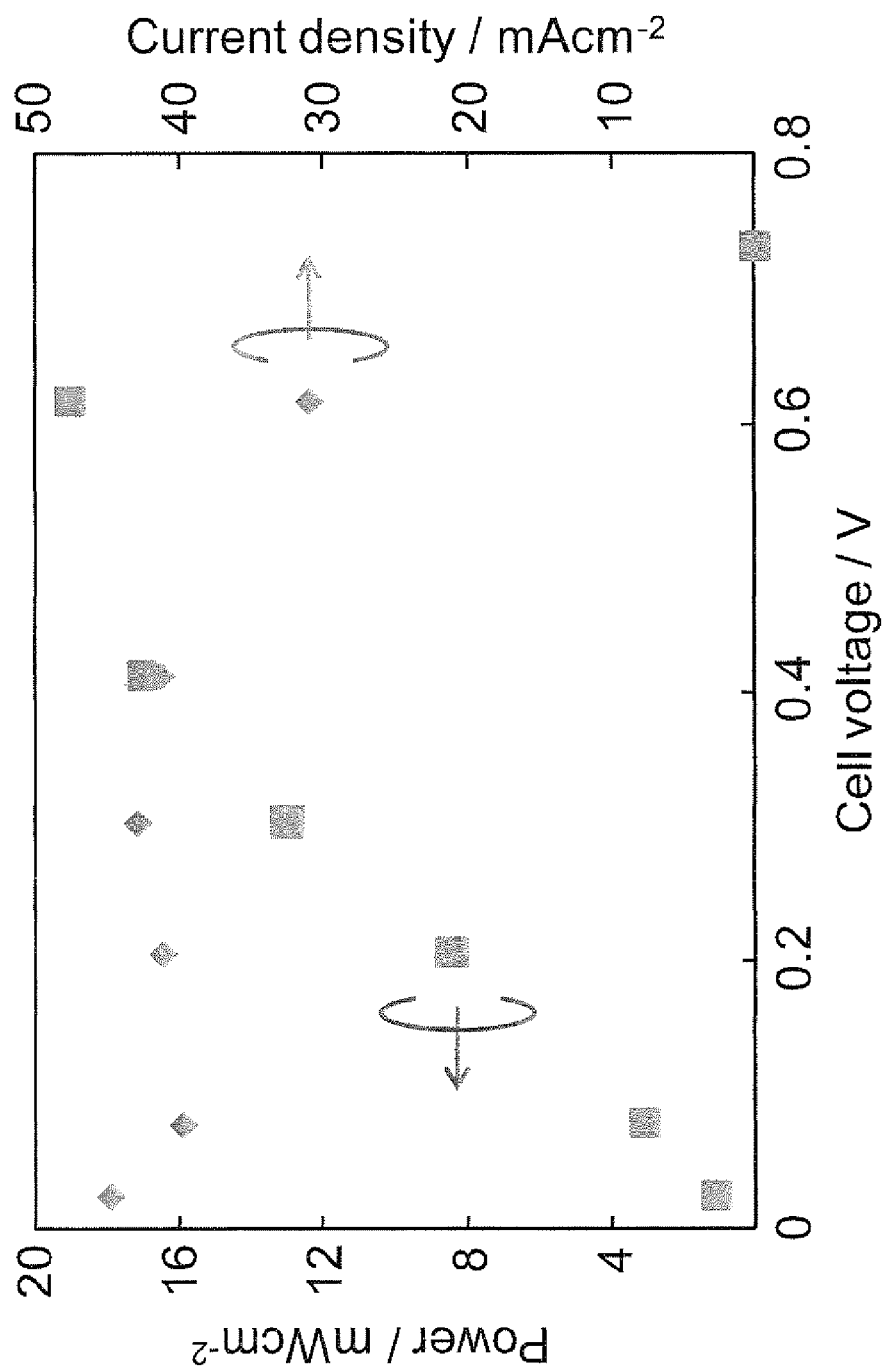
FIG. 11 shows an output evaluation result of a bio power generation device.

A bio-power generating device was prepared using the constricted carbon nanotube film 530 using the stirring inclusion method in example 5 and example 9 described above, different external resistors (10 kΩ~2 MΩ) were connected between electrodes, a voltage at this time was measured using an electrochemical measurement system (Electrochemical Analyzer Model 600S, manufactured by BAS) and current and output were measured. The measurement conditions were 200 mM of an oxygen saturated fructose solution. The results are shown in FIG. 11. It was possible to obtain a maximum output density of 19 µW/cm$^3$ at a voltage of 0.61 V using the bio-power generating device related to the present example.

(Winding on a Wire Electrode and LED Lighting Test)

Figure 12:
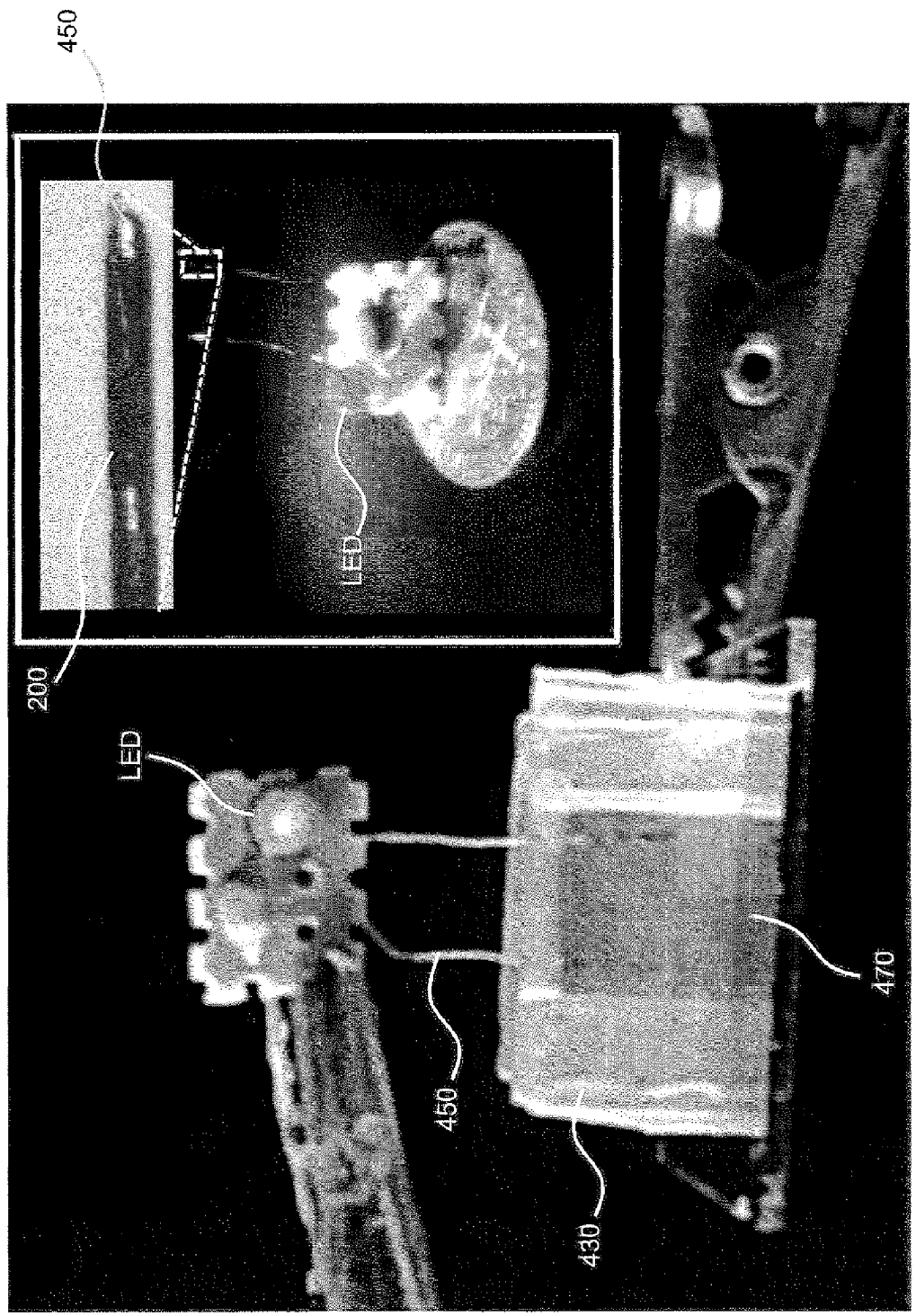
FIG. 12 shows an LED device related to one example of the present invention.

Furthermore, the carbon nanotube film described above was wound onto a wire electrode and a lighting test of an LED was performed. In the present example, a condenser (1 µF) and a red LED were bonded to a charge pump IC S-882Z20, manufactured by Seiko Instruments). The assembled device was sealed using Polydimethylsiloxane (PDMS). The LED device related to the present example is shown in FIG. 12. The carbon nanotube film 200 was wound onto a gold wire 450 (diameter 0.2 mm) extending from the device. The carbon nanotube film prepared the same as in the example described above was moistened in a buffer solution and wound onto the wire 450 using tweezers. After drying in an atmosphere under room temperature, 200 mM of a fructose solution was filled into a container 430 as a fuel 470 and lighting of the LED was confirmed by immersing the gold wire 450 in the fuel 470.

(Evaluation of a Biosensor)

An example of a biosensor of the present invention explained in the third embodiment is shown in FIG. 9 and FIG. 10. It is possible to evaluate FIG. 9 and FIG. 10 as a biosensor using the carbon nanotube films in each example and the non-orientated CNT in the comparative example. That is, each example and comparative example shows a biosensor which detects fructose in FIG. 9 and oxygen in FIG. 10.

Here, example 6 in FIG. 9 is an example of detecting a buffer solution which not include fructose using the carbon nanotube film 520 which is not constricted using the stirring inclusion method in example 4, an example 10 in FIG. 10 is an example of detecting a buffer solution in which nitrogen ($N_2$) is saturated using the carbon nanotube film 520 which is not constricted using the stirring inclusion method in example 8. From this result it can be seen that the carbon nanotube film related to the present invention of the present example functions as a highly sensitive biosensor.

(Theoretical Predication of an Amount of Enzyme Inclusion)

Figure 13:
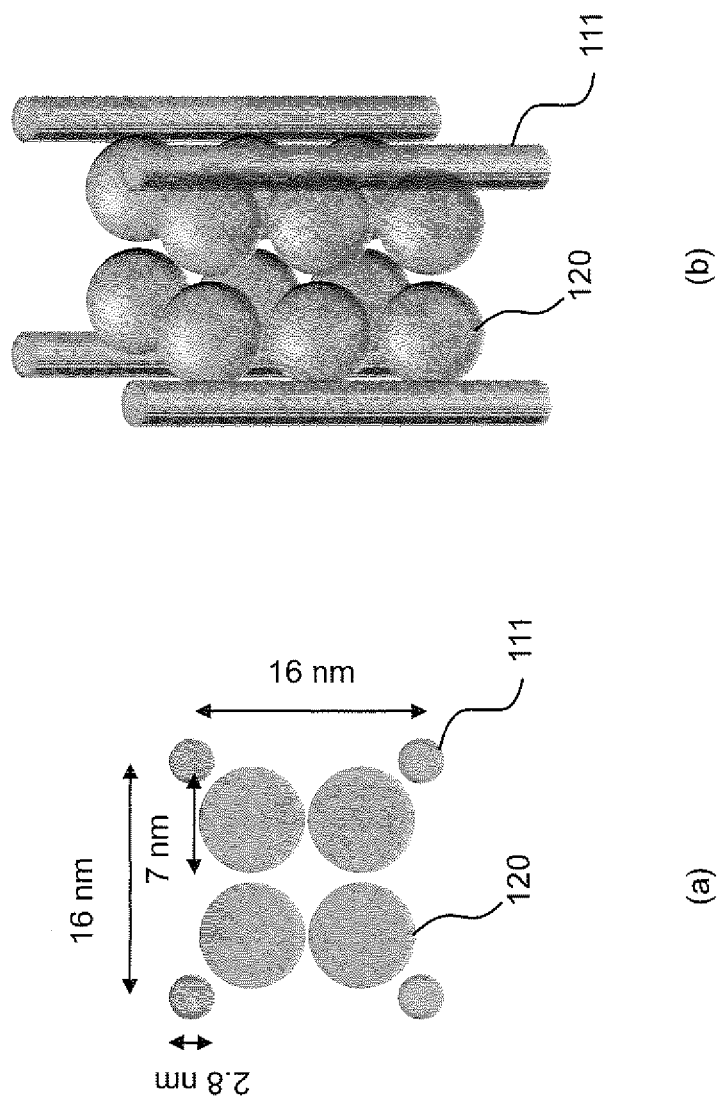
FIG. 13 is an exemplary view showing a theoretical spatial arrangement between a carbon nanotube aggregate 110 and an enzyme 120 (a) is an upper surface view and (b) is a perspective view.

In the carbon nanotube film related to the present invention, a theoretical evaluation of the included amount of fructose dehydrogenase, (FDH, molecular weight: ca. 140 kDa) in a carbon nanotube aggregate 110 (1 mm×12 µm×1 mm) was performed. As is shown in FIG. 13 (a) and FIG. 13 (b), in the carbon nanotube film before drying, the carbon nanotube aggregate 110 included CNTs 111 with a diameter of 2.8 mm arranged at intervals of 16 nm with multiple spaces existing therein. The number (Nenz) which can include FDH (enzyme 120) with a diameter of 7 nm with respect to these spaces is expressed in formula (1)

[formula 1]

$$N_{enz}=4(H/r)(S/U) \qquad (2)$$

Here, H=1.0 mm (CNT length), R=7.0×10$^{-6}$ mm (FDH diameter), S=12×10$^{-3}$ mm$^2$ (bottom surface area of the carbon nanotube aggregate 110), and U=2.6×10$^{10}$ mm$^2$ mm (bottom surface area of a space enclosed by a 16 nm interval). From this result the maximum amount of FDH included in the carbon nanotube aggregate 110 (1 mm×12 µm×1 mm) before drying was calculated as 6.2 µg from the relationship between the molecular weight of FDH and Avagado number.

(Actual Measurement of the Amount of Included Enzyme)

In the carbon nanotube film related to the present invention, an evaluation of the included amount of fructose dehydrogenase, (FDH, molecular weight: ca. 140 kDa) in a carbon nanotube aggregate 110 (1 mm×12 µm×1 mm) was performed by way of experiment. The amount of included FDH was measured using a Protein Quantitation Kit (C-6667, manufactured by Molecular Probes). Inclusion of an enzyme in the carbon nanotube aggregate 110 was performed using the stirring method shown previously. The carbon nanotube aggregate (CNTF) included with an enzyme was immersed in a sodium phosphate water solution (including 0.1 M sodium borate, 1% of sodium cholate, pH 9.3) and dispersed using an ultrasonic homonegizer. Following this, CBQCA was labeled on the FDH using 5 mM (3-(4-carboxybenzoyl)-quinoline-2-carboxaldehyde (ATTO-TAG CBQCA) referred to below as CBQCA) and 20 mM KCN. The fluorescence intensity was measured following 1.5 hours of incubation and the amount of FDH was calculated from a calibration curve calculated in advance.

Figure 14:
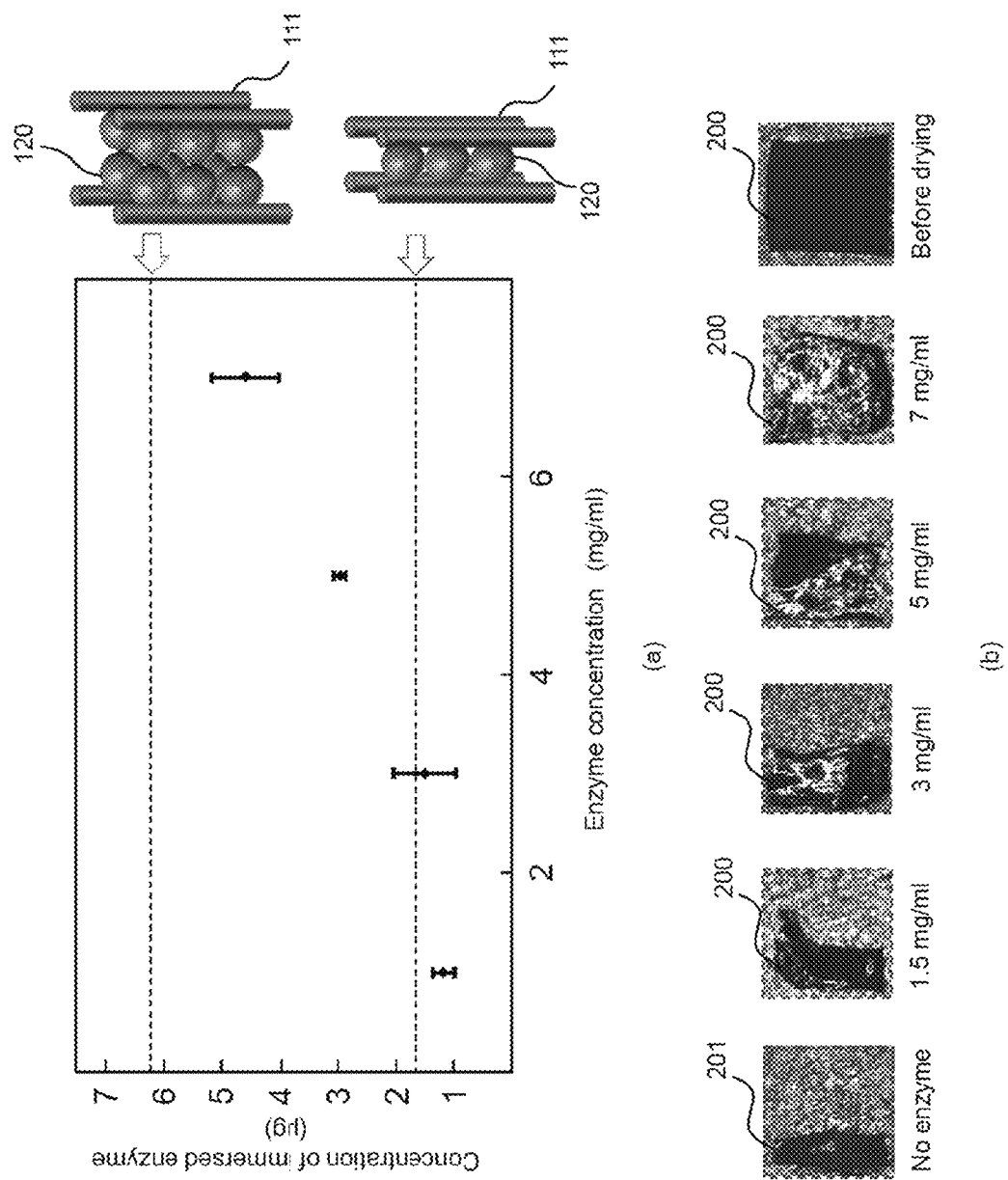
FIG. 14 shows an actual measurement result of the amount of contained enzyme (a) shows the relationship between enzyme concentration and the amount of contained enzyme and (b) is optical microscopic image.

The measurement results are shown in FIG. 14 (a). As is clear from FIG. 14 (a), the amount of enzyme included in the carbon nanotube film 100 increased with an increase in the immersed enzyme concentration. In addition, it was clear from the optical microscopic image shown in FIG. 14 (b) that the constriction of the carbon nanotube film 200 was controlled with an increase in the included amount of the enzyme. That is, it is possible to control the included amount of an enzyme in a carbon nanotube film by the concentration of an immersed enzyme.

(Evaluation of Enzyme Concentration and Electrode Capabilities)

Figure 15:
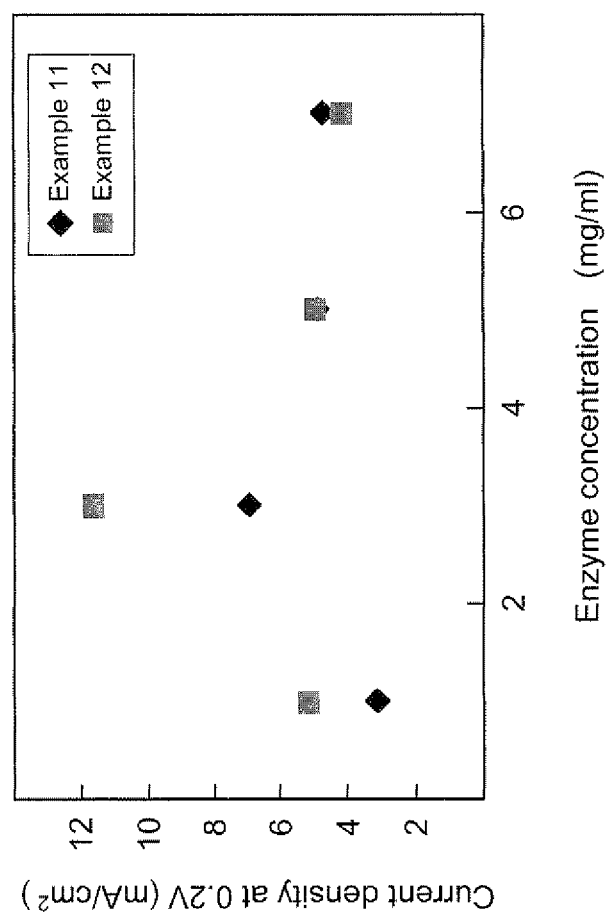
FIG. 15 shows the relationship between enzyme concentration and current density.

Next, the relationship between the concentration of an immersed enzyme and the electrode capabilities of a carbon nanotube film were examined. A non-constricted carbon nanotube film 610 including FDH used in the actual measurement of an amount of included enzyme was used as example 11 and a constricted carbon nanotube film 630 including FDH was used as example 12 in the measurement of current density. FIG. 15 shows the relationship between the concentration of an immersed enzyme and current density. From the results in FIG. 15, the current density of the carbon nanotube film was largest in both example 11 and example 12 under a condition where FDH was included in the carbon nanotube aggregate 110 with an enzyme concentration of 3 mg/ml. As is shown in FIG. 14 (a), the FDH concentration matched a theoretical value calculated from a model in which FDH were densely arranged in one column parallel to the length direction of the CNT 111 in a space enclosed by 4 CNTs 111 in the carbon nanotube aggregate.

However, the current density of the carbon nanotube film dropped when FDH was included in the carbon nanotube aggregate 110 with an excess enzyme concentration which exceeds 3 mg/ml. From this result, it is inferred that the electrode capabilities per unit area dropped when the constriction of the carbon nanotube film is controlled in a drying process and miniaturization of the carbon nanotube film is obstructed when FDH was included in the carbon nanotube aggregate 110 with an excess enzyme concentration which exceeds 3 mg/ml. In addition, it is inferred that inclusion of FDH at an excessive enzyme concentration causes changes in the orientation of an enzyme included in the carbon nanotube film and a drop in electrode capabilities due to a loss of activity of the enzyme. Therefore, in the carbon nanotube film related to the present invention, electrode capabilities become optimum per unit area by including a structure in which the enzyme 120 is arranged in one column in a parallel direction to the length direction of the CNT 111 in a space enclosed by 4 CNTs 111 of the carbon nanotube aggregate. It is possible to optimize electrode capabilities in the carbon nanotube film related to the present invention by adjusting the concentration of immersed enzyme.

(Durability Evaluation of an Enzyme Electrode)

Figure 16:
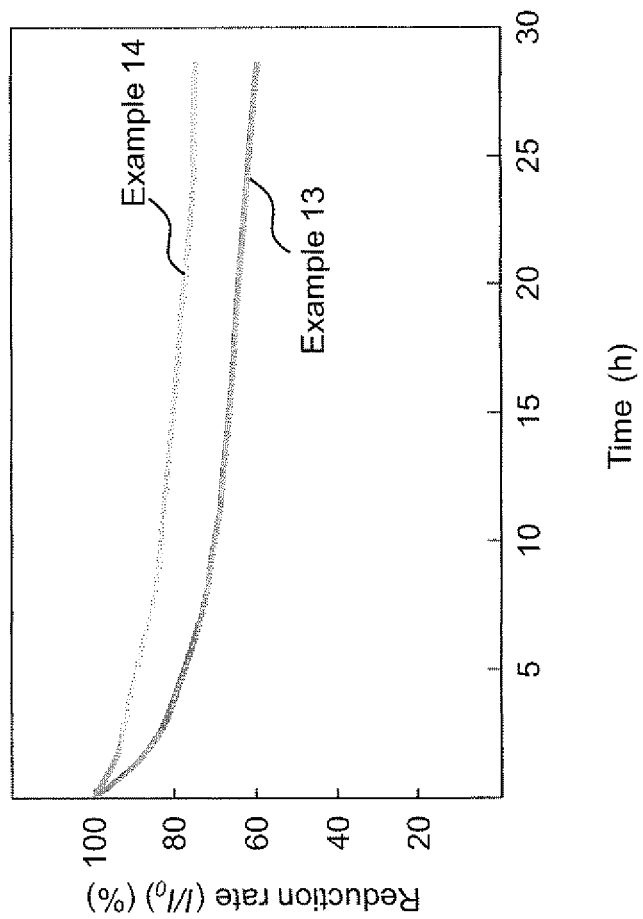
FIG. 16 shows the result of a durability evaluation of an enzyme electrode.

Durability of an enzyme electrode was evaluated using a carbon nanotube film included with FDH in a 3 mg/ml solution as example 13 and a carbon nanotube film with this constricted as example 14. The durability evaluation was performed by measuring an oxidation current (0.2 V, reference: Ag/AgCl) in a McIlvaine buffer (pH 5.0) including 200 mM fructose and calculating a temporal reduction rate with respect to an initial current. As is clear from FIG. 16, after 28 hours from the start of the measurement output current dropped 41% in example 13, however, output current dropped only 25% in example 14. From this result it is inferred that nano-level spaces in the carbon nanotube film constricted by the drying process contributed to enzyme maintenance and activity support.

(Correlation between Fructose Concentration and Current Density)

Figure 17:
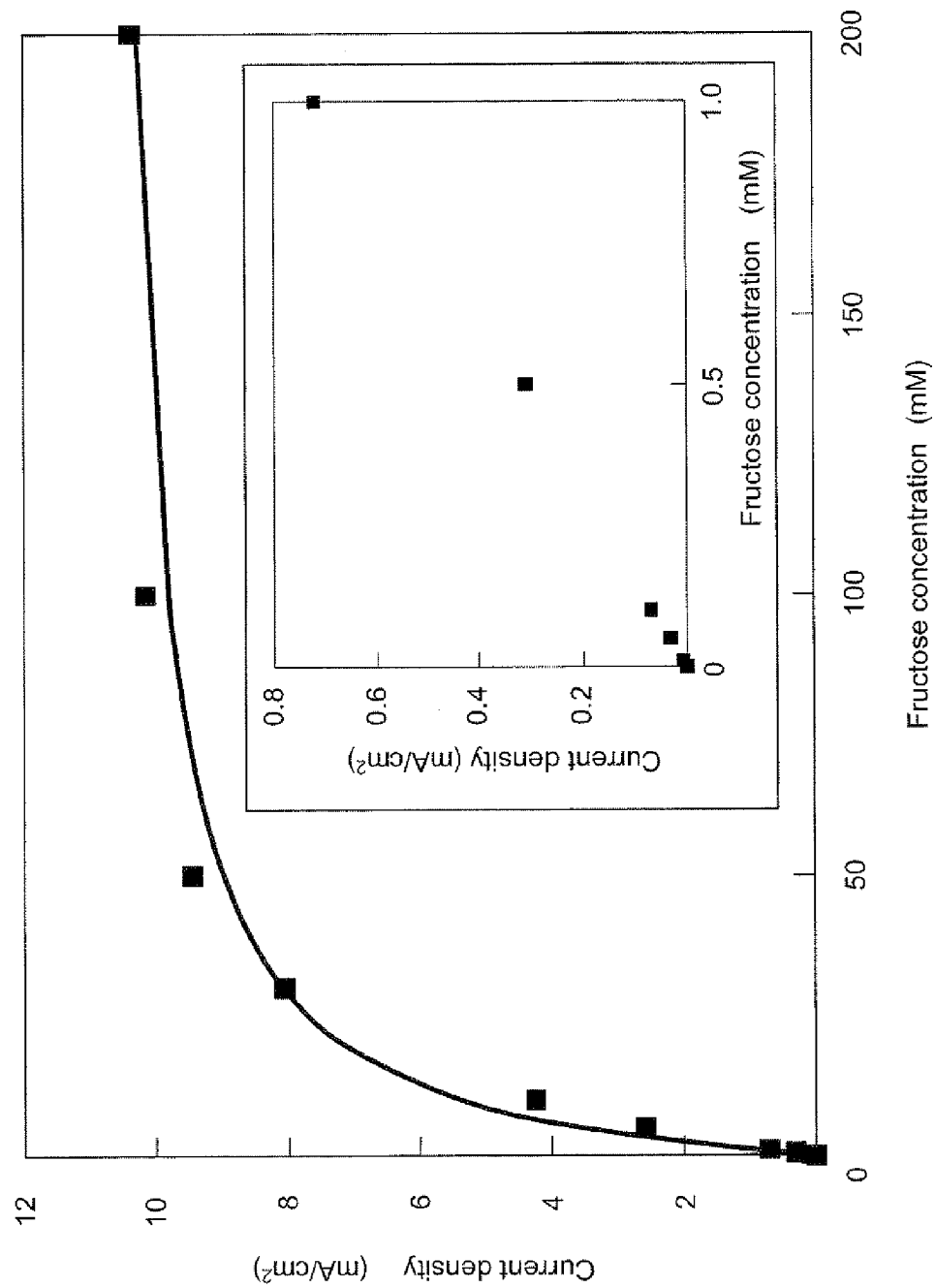
FIG. 17 shows the relationship between fructose concentration and current density.

Current density was measured in a fructose solution with different concentrations and the capabilities of a biosensor electrode of the carbon nanotube film related to the present invention were evaluated. The measurement results of current density are shown in FIG. 17. An actual measurement value was fitted into a Lineweaver-Burke equation (3) and a Michaelis Menten coefficient (Lm, app) was calculated.

[Formula 2]

$$\frac{1}{I_{ss}} = \frac{1}{I_{max}} + \frac{K_{m,app}}{I_{max}}\left(\frac{1}{C}\right) \quad (3)$$

Here, Iss is the current density in a fructose concentration (C) and Imax is a maximum current density.

From the measurement results, Km, app showed 10±1 mM and this matches a value measured when an enzyme is in a bulk state dispersed in a solution. That is, it is clear that enzyme activity is maintained even when the carbon nanotube film related to the present invention is constricted. In addition, because the detection limit of fructose is 10 μM and a linear correlation is shown with current density at a fructose concentration up to around 50 mM, it is clear that the carbon nanotube film related to the present invention includes excellent capabilities even as a biosensor.

(Evaluation of a Stacked Carbon Nanotube Film and Electrode Capabilities)

It was evaluated whether electrode capabilities are improved by stacking the carbon nanotube films described above. An anode was evaluated applying a McIlvaine buffer (pH 5.0) including 200 mM of fructose to two constricted stacked carbon nanotube films as example 15, one constricted stacked carbon nanotube film as example 16, one non-constricted stacked carbon nanotube film as example 17, and a non-constructed carbon nanotube film with no fructose added as comparative example 7, which were immersed in 3 mg/ml of a solution and included with FDH.

Figure 18:
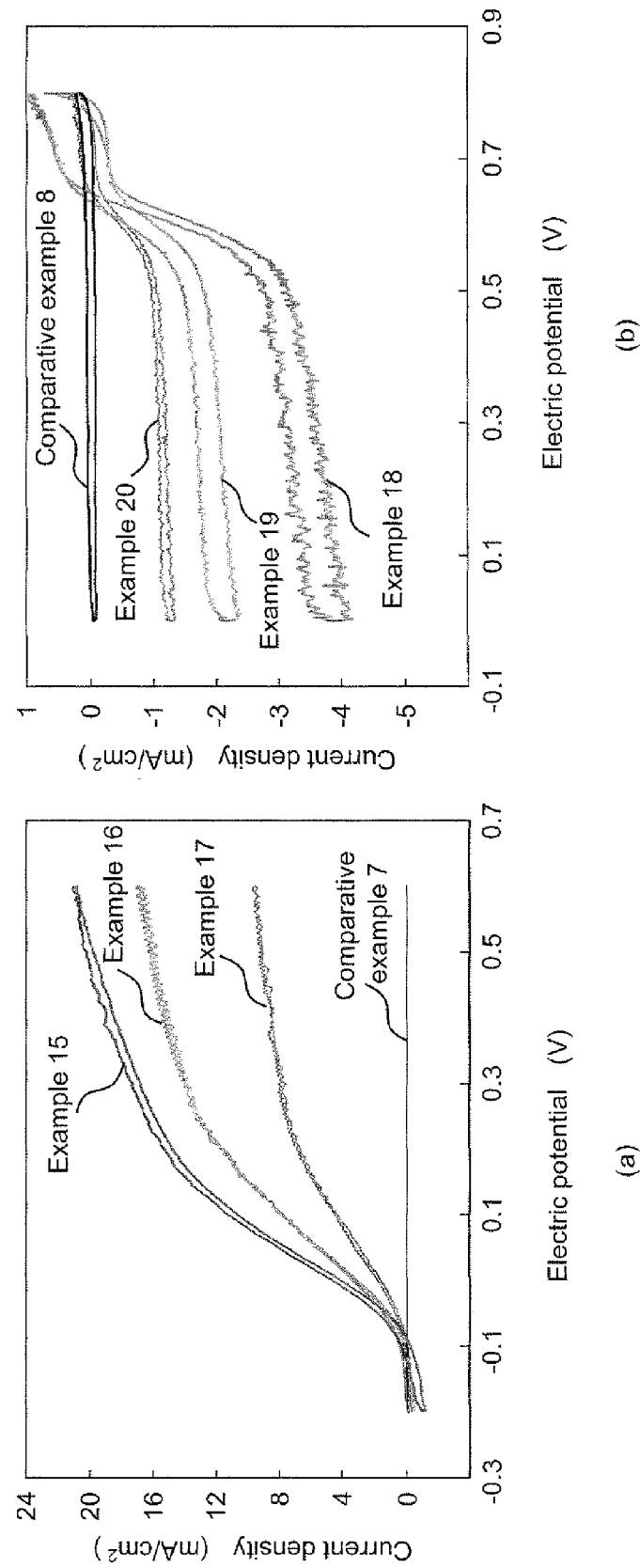
FIG. 18 shows the relationship between a stacked carbon nanotube film and electrode capabilities (a) shows a measurement result of an anode and (b) shows a measurement result of a cathode.

The measurement results are shown in FIG. 18 (a). It was clear that electrode capabilities in example 15 in which two constricted carbon nanotubes films were stacked improved compared to example 16 in which only one constricted carbon nanotube film was used.

In addition, similarly, an cathode was evaluated by preparing two constricted stacked carbon nanotube films as example 18, one constricted carbon nanotube film as example 19, and one non-constricted stacked carbon nanotube film as example 20 which were immersed in 0.25 mg/ml of a solution and included with Laccase, and a McIlvaine buffer (pH 5.0) with saturated oxygen was used as the measurement solution. A McIlvaine buffer (pH 5.0) saturated with nitrogen was used in the measurement of a non-constricted carbon nanotube film as comparative example 8.

The measurement results are shown in FIG. 18 (b). It was clear that electrode capabilities in example 18 in which two constricted carbon nanotubes films were stacked improved compared to example 19 in which only one constricted carbon nanotube film was used.

(Evaluation of Battery Output)

Figure 19:
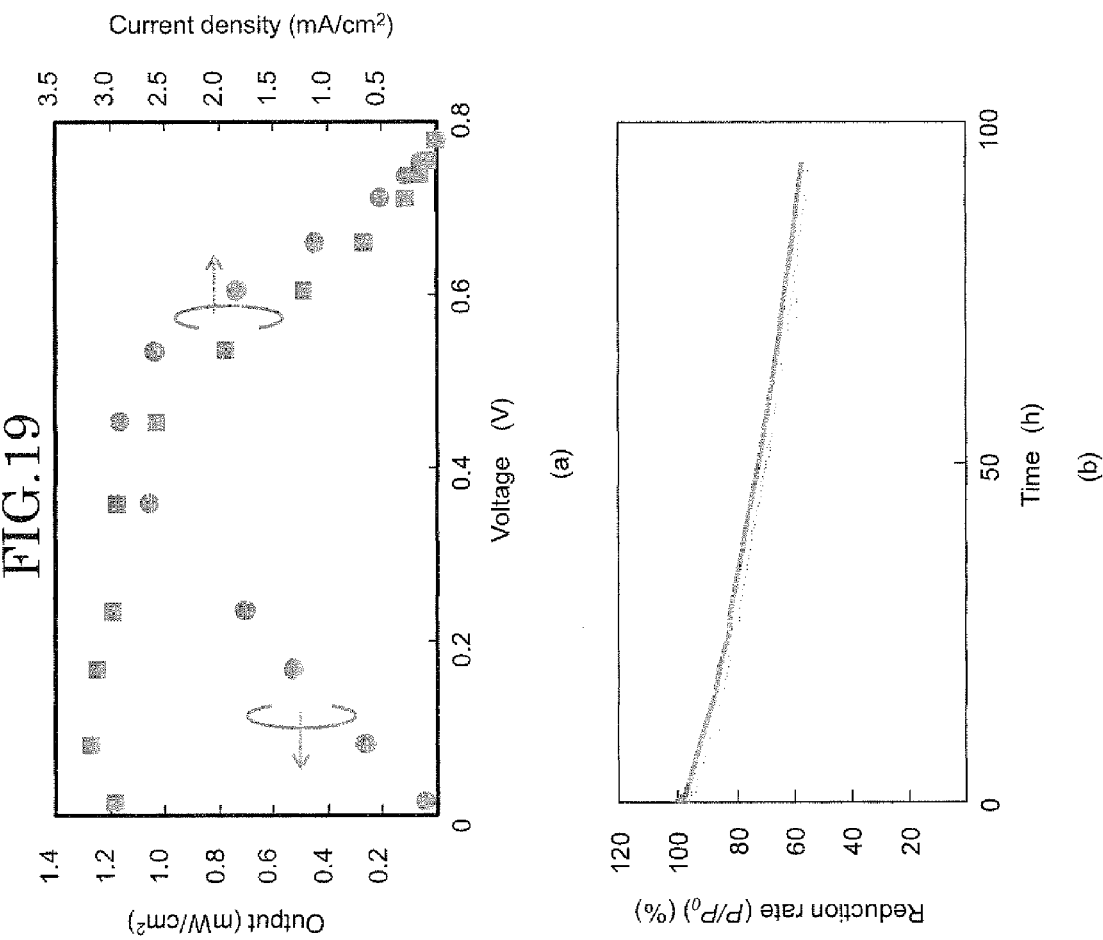
FIG. 19 shows a result of capabilities evaluation of a battery (a) shows a measurement result output with respect to a voltage of the battery and current density and (b) shows the result of a durability experiment.

An evaluation of battery output was performed using the two stacked constricted carbon nanotube films in example 15 and example 18 described above. The output measurement was carried out in a McIlvaine buffer (pH 5.0) including 200 mM of fructose. The measurement results of output and current density with respect to battery voltage are shown in FIG. 19 (a). In the present example, an output of 1.16 mW/cm² was obtained when voltage was 0.45V. An open circuit voltage and maximum current density were 0.77V and 3.2 mA/cm² respectively.

(Durability Evaluation of a Battery)

Furthermore, durability of the above described battery was evaluated. The evaluation of the battery was performed by measuring an oxidation current (0.2V, reference: Ag/AgCl) in a McIlvaine buffer (pH 5.0) including 200 mM of fructose and by calculating a temporal reduction rate with respect to an initial power. As is shown in FIG. 19 (b), the battery in the present example could maintain a power of 80% even after 37 hours had elapsed from the start of the measurement.

(Evaluation of a Carbon Nanotube Film Structure and Electrode Capabilities)

Figure 20:
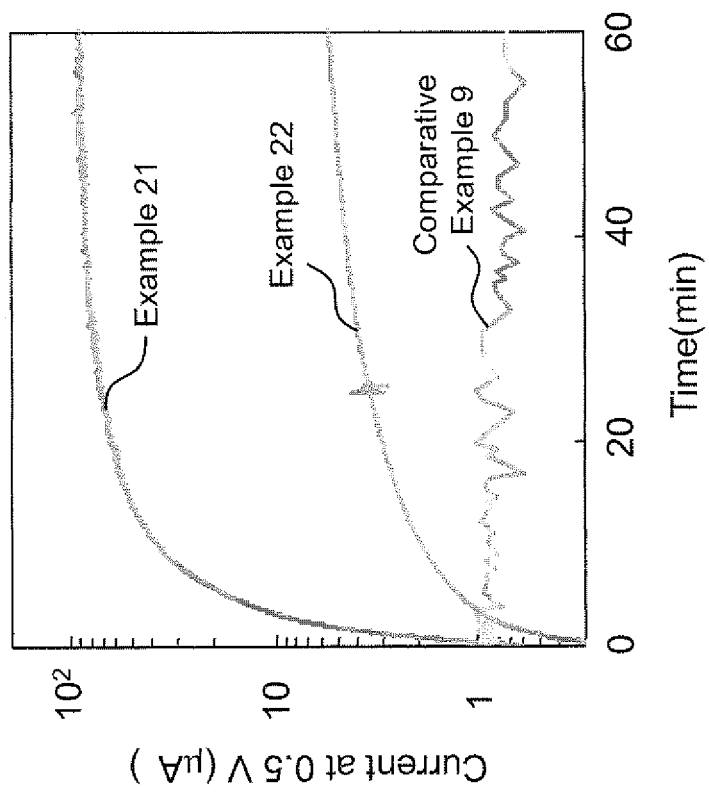
FIG. 20 shows the effects on electrode capabilities by the structure of a carbon nanotube film.

The structure of a carbon nanotube and effects on electrode capabilities was evaluated. The electrode was immersed in a stirred mixed solution (200 mM fructose buffer solution, 3 mg/ml FHD) using 3 types (carbon nanotube aggregate not constricted in pre-processing (example 21), carbon nanotube aggregate constricted in pre-processing (example 22) and a non-orientated CNT with a length of 1 mm (comparative example 9). FIG. 20 shows the oxidation current of a fructose obtained in a three electrode method (working: carbon nanotube electrode, reference: Ag/AgCl sat. KCL, counter: platinum) using an electrochemical measurement system (Electrochemical Analyzer Model 600S, manufactured by BAS), and measured at a constant voltage (0.5V).

The carbon nanotube aggregate constricted by pre-processing in example 22 held about the same capacitance volume as the carbon nanotube aggregate (example 2) which is not constricted by pre-processing as is shown in FIG. 8 (b). However, because it is difficult to incorporate a nano-size enzyme one a space has been constricted, the fructose oxidation current was smaller by single figures. In addition, the current density of non-orientated CNT in comparative example 9 was smaller again by single digits.

(Evaluation of the Quality of a Carbon Nanotube Film and Electrode Capabilities)

Figure 21:
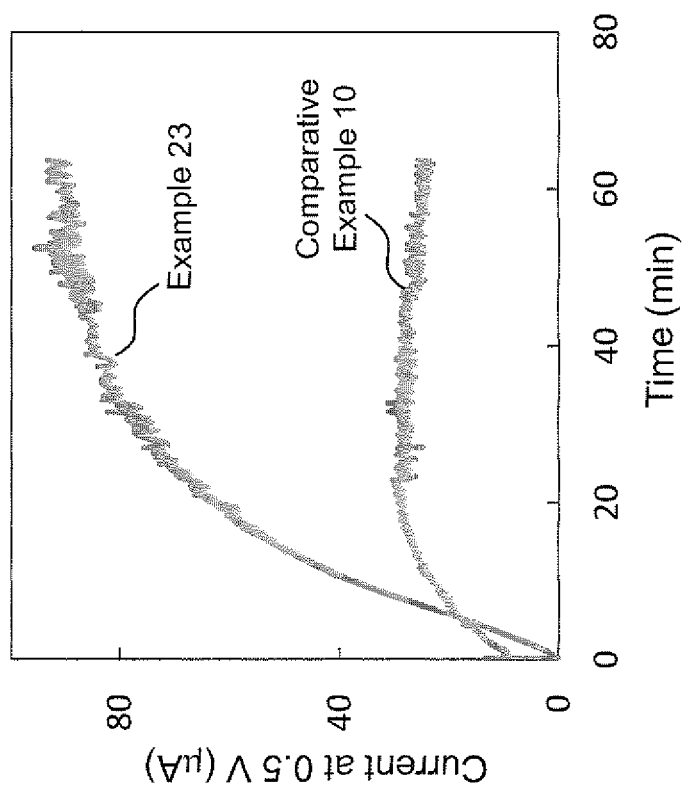
FIG. 21 shows the relationship between the G/D ratio of a carbon nanotube film and electrode capabilities.

The quality of a carbon nanotube film and effects on electrode capabilities were evaluated. The electrode was immersed in a stirred mixed solution (200 mM fructose buffer solution, 3 mg/ml FHD) using 2 types (carbon nanotube aggregate (comparative example 10) with a G/D ratio of 1, and a carbon nanotube aggregate (example 23) with a G/D ratio of 4). FIG. 21 shows the oxidation current of a fructose obtained in a three electrode method (working: carbon nanotube electrode, reference: Ag/AgCl sat. KCL, counter: platinum) using an electrochemical measurement system (Electrochemical Analyzer Model 600S, manufactured by BAS), and measured at a constant voltage (0.5V).

The G/D ratio shows the ratio of a G band and D band in a Raman spectrum and shows higher crystallization (fewer defects) the greater the value. As is shown in FIG. 12, the electrode capabilities were better in the carbon nanotube aggregate with the higher G/D ratio.

(Evaluation of Capabilities of a Cathode with Bilirubin Oxidase as an Electrode Catalyst)

Figure 22:
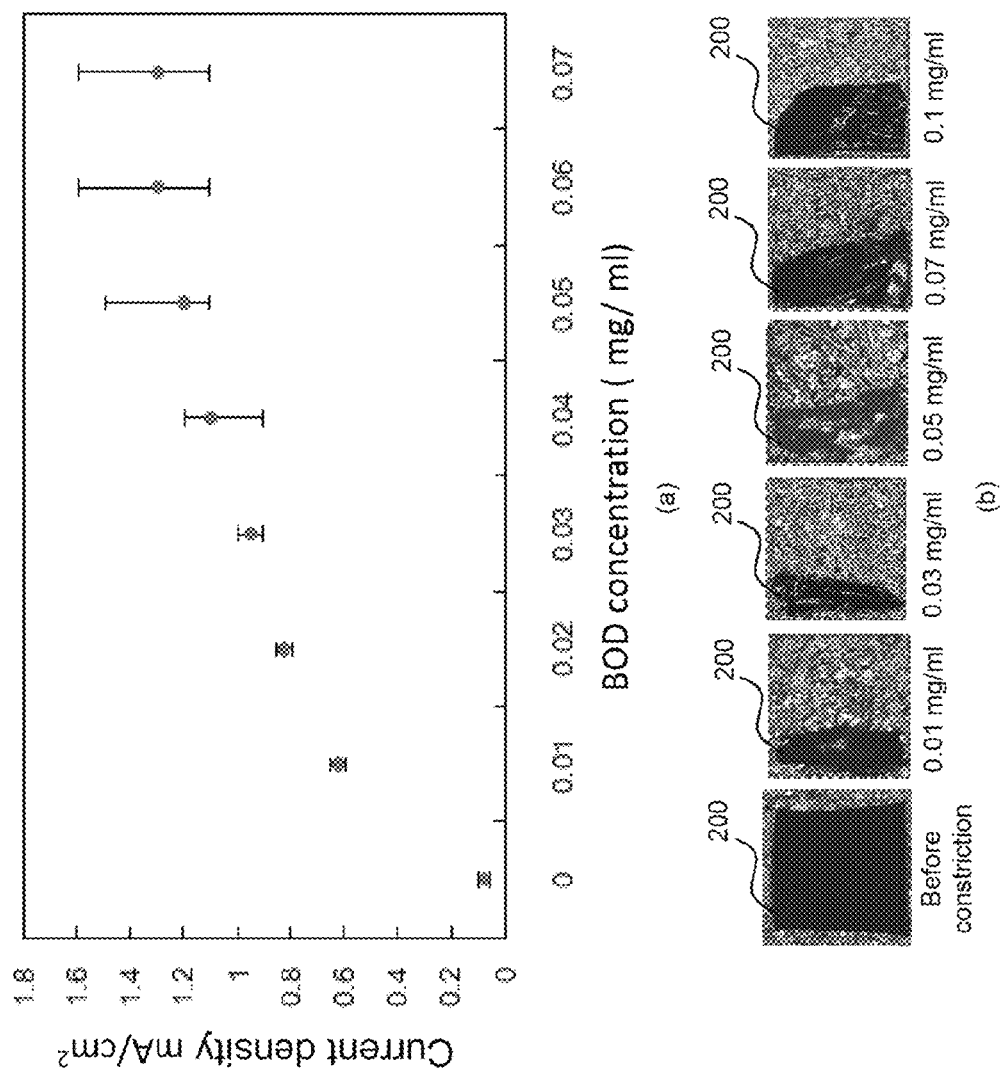
FIG. 22 (a) shows the capabilities of a cathode which uses bilirubin oxidase as an electrode catalyst and (b) shows the relationship between the concentration of a bilirubin oxidase solution and contraction of a carbon nanotube aggregate.

A carbon nanotube film in which bilirubin oxidase (BOD) known as multicopper oxidase is used as a catalyst was prepared and capabilities were evaluated. First, the relationship between the concentration of a BOD solution to be immersed in and the capabilities of the carbon nanotube film were examined. A carbon nanotube aggregate 110 not constricted by pre-processing was used in a current density evaluation. FIG. 22 (a) shows the relationship between concentration of the BOD solution to be immersed in and current density. A current value increased in response to an increase in the concentration of the BOD solution and saturated at a BOD concentration of about 0.05 mg/ml or more. The appearance of constriction of a carbon nanotube film 250 which includes this BOD was observed using an optical microscope (FIG. 22 (b)). As is clear from the observation results, the level of constriction depends on the concentration of the BOD solution in which the carbon nanotube film is immersed. The constriction of the film saturated at 0.05 mg/ml or more which half an initial area. This matches a model in which BOD size was assume to be about 2 nm and a CNT surface was saturated with the BOD.

Figure 23:
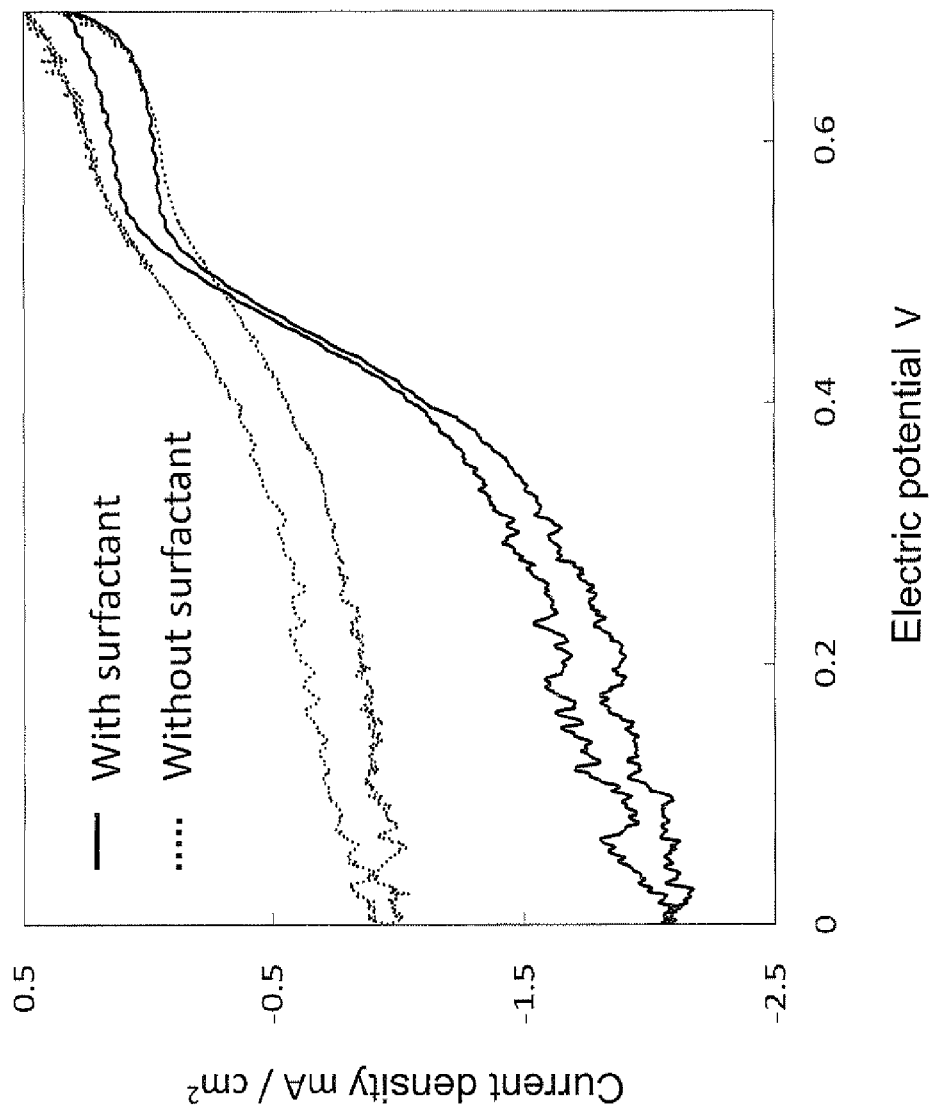
FIG. 23 shows the effects of a surfactant agent on electrode capabilities.

Next, the effects of a surfactant on the capabilities of the carbon nanotube film 250 included with BOO was examined. An oxidation-reduction current, potential curve is shown in FIG. 23. It is clear that surface modification of a nanotube by a surfactant is important for the activity of an enzyme. This is assumed to reduce drying out of a water component in the constriction process by modification of the surfactant on the CNT surface which is originally hydrophobic. As a result, a maximum current density of 2.0 mA/cm$^2$ at 0V vs, Ag/AgCl was obtained.

As explained above, according to the present invention, a safe, small scale and flexible, free-standing type protein containing carbon nanotube film is provide and a sensor and power generating device with excellent functions are provided by using the carbon nanotube film.

According to a method of the present invention, a safe, small scale and flexible, free-standing type protein containing carbon nanotube film, and a sensor and power generating device each equipped with the carbon nanotube film as an electrode are provided.

The invention claimed is:

1. A carbon nanotube film comprising:
    a carbon nanotube aggregate formed by aggregating a plurality of carbon nanotubes with a plurality of enzymes,
    wherein the plurality of enzymes included exists among the plurality of carbon nanotubes.
2. The carbon nanotube film according to claim 1, wherein a different protein to the enzyme is included.
3. The carbon nanotube film according to claim 1, wherein a surfactant is included between the plurality of carbon nanotubes.
4. The carbon nanotube film according to claim 1, wherein a plurality of mediator molecules is included between the plurality of carbon nanotubes.
5. The carbon nanotube film according to claim 1, wherein the enzyme is an oxidase or a dehydrogenase.
6. The carbon nanotube film according to claim 1, wherein the carbon nanotube aggregate includes a surface area of 600 m$^2$/g or more and 2,600 m$^2$/g or less, a weight density of 0.002 g/cm$^3$ or more and 0.2 g/cm$^3$ or less, and a pore size distribution maximum of 5 nm or more and 100 nm or less.
7. The carbon nanotube film according to claim 1, wherein a part is included in which the enzyme is arranged in one column in a parallel direction to a length direction of the carbon nanotube at a space enclosed by 4 of the carbon nanotubes of the carbon nanotube aggregate.

* * * * *